US012564615B2

(12) United States Patent

Alasoom

(10) Patent No.: US 12,564,615 B2

(45) Date of Patent: Mar. 3, 2026

(54) TREATMENT METHOD FOR CARDIAC HYPERTROPHY

(71) Applicant: Imam Abdulrahman Bin Faisal University, Dammam (SA)

(72) Inventor: Lubna Ibrahim A. Alasoom, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 261 days.

(21) Appl. No.: 18/544,633

(22) Filed: Dec. 19, 2023

(65) Prior Publication Data

US 2024/0148813 A1     May 9, 2024

Related U.S. Application Data

(62) Division of application No. 17/406,895, filed on Aug. 19, 2021, now abandoned.

(51) Int. Cl.

| *A61K 36/71* | (2006.01) |
|---|---|
| *A61K 9/00* | (2006.01) |
| *A61K 45/06* | (2006.01) |
| *A61P 9/00* | (2006.01) |

(52) U.S. Cl.

CPC ............ *A61K 36/71* (2013.01); *A61K 9/0053* (2013.01); *A61K 45/06* (2013.01); *A61P 9/00* (2018.01)

(58) Field of Classification Search

None

See application file for complete search history.

(56) References Cited

U.S. PATENT DOCUMENTS

| 8,535,740 B2 | 9/2013 | Babish et al. |
|---|---|---|
| 10,588,930 B2 | 3/2020 | Al Asoom |
| 2005/0215533 A1 | 9/2005 | Gottlieb |
| 2005/0261257 A1 | 11/2005 | Vermeer |
| 2005/0267143 A1 | 12/2005 | Davis |
| 2011/0244060 A1 | 10/2011 | Ismail et al. |
| 2019/0030110 A1 | 1/2019 | Al Asoom |

OTHER PUBLICATIONS

Al-Asoom et al. (Cardiovascular Toxicology, 14: 243-250, 2014).*

Pop, et al. ; Nigella sativa: Valuable perspective in the management of chronic diseases ; Iranian Journal of Basic Medical Sciences vol. 23, No. 6 ; Jun. 2020 ; 15 Pages.

Jaarin, et al. ; Mechanisms of the antihypertensive effects of Nigella sativa oil in L-Name-induced hypertensive rats ; Clinics 2015 ; Sep. 9, 2015 ; 7 Pages.

Hebi, et al. ; Cardiovascular effect of *Nigella sativa* L. Aqueous Extract in Normal Rats ; Cardiovascular & Haematological Disorders-Drug Targets, 2016, 16 ; pp. 47-55 ; 9 Pages.

Rahma, et al. ; Effect of a black cumin (*Nigella sativa*) ethanol extract on placental angiotensin II type 1-receptor autoantibody (AT1-AA) serum levels and endothelin-1 (ET-1) expression in a preeclampsia mouse model ; Journal of Taibah University Medical Sciences (2017) 12(6) ; pp. 528-533 ; 6 Pages.

Jafar, et al. ; Investigation of the Effects of Nigella Sativa on serum levels of IL-6 and TNF-α in Women Athletes ; International Journal of Humanities and Social Science, vol. 9, No. 12 ; Dec. 2019 ; 8 Pages.

Kiefer et al. (Current Pharmaceutical Design, 2003, 9, 1733-1744).

* cited by examiner

*Primary Examiner* — Bong-Sook Baek

(74) *Attorney, Agent, or Firm* — Oblon, McClelland, Maier & Neustadt, L.L.P.

(57) ABSTRACT

A method for reducing pathological cardiac hypertrophy and/or inducing physiological cardiac hypertrophy by administering *Nigella sativa* or an extract thereof to a subject in need thereof, especially to an athletic subject in order to reduce exercise-induced pathological cardiac hypertrophy. A composition comprising *Nigella sativa* for use in said method.

9 Claims, 24 Drawing Sheets

TREATMENT METHOD FOR CARDIAC HYPERTROPHY

CROSS-REFERENCE TO RELATED APPLICATION

The present application is a Division of U.S. application Ser. No. 17/406,895, pending, having a filing date of Aug. 19, 2021.

STATEMENT REGARDING PRIOR DISCLOSURES BY THE INVENTOR OR A JOINT INVENTOR

Aspects of this technology are described by Al Asoom, et al. EVIDENCE-BASED COMPLEMENTARY AND ALTERNATIVE MEDICINE, Apr. 9, 2021, Article ID 5553022, incorporated herein by reference in its entirety.

BACKGROUND OF THE INVENTION

Field of the Invention

The invention pertains to the fields of medicine, cardiology, and exercise science, especially to a method for inducing beneficial adaptive responses to exercise using *Nigella sativa*.

Description of the Related Art

Cardiac hypertrophy is an adaptive response of the heart to an increase in volume or stress load. It is characterized by an increase in the thickness of the left ventricle which is attributed to the enlargement of cardiomyocytes; Shimizu, I, et al., J. MOL. CELL. CARDIOL. 2016, 97, 245.

Clinical and experimental observations have identified two forms of cardiac hypertrophy: the first one is precipitated by pathological insults such as stress overload due to hypertension, valvular heart disease, or injury of the cardiac muscle due to ischemia and infarction (namely, pathological cardiac hypertrophy), whereas the other one (namely, physiological cardiac hypertrophy) develops as a consequence of moderate volume and stress overload induced by chronic exercise training; Nakamura, M. et al., NATURE REV. CARDIOLOGY 2018, 15(7), 387. Pathological cardiac hypertrophy typically results from damage to the heart while physiological cardiac hypertrophy strengthens or increases the capacity of the heart.

In pathological heart hypertrophy, initial adaptive responses to a pathological insult are brought about to enhance the cardiac contractility and maintain the functional requirement of the heart. However, as an insult persists, it overwhelms some of the compensatory pathways and deviates into undesirable changes. Ventricular volume overload is manifested by increased left atrial pressure, left ventricular and end-diastolic and stroke volumes. The resulting cardiac remodeling precipitates multiple faulty structural, electrical, and biochemical modifications that downgrade the function of the heart; McMullen, J. R. et al, CLIN, EXP. PHARMA PHYSIOL. 2007, 34(4), 255.

In contrast, physiological cardiac hypertrophy initiated by moderate volume overload of physiological origin such as exercise training advantageously maintains cardiac function and provides multiple favorable structural, electrical, and biochemical remodelings that enhance cardiac function; Schuttler, D. et al., CELLS, 2019, 8(10).

Two distinguishable molecular pathways characterize pathological or physiological cardiac hypertrophy: one undesirable, the other advantageous.

Pathological hypertrophy is mediated through the G-protein-coupled receptor (GPCR) pathway. The main precursors of the GPCR pathway are angiotensin-II, endothelin-1, and catecholamine. Its intracellular cascades involve multiple mitogen-activated protein kinase MAPK enzymes such as Erk1/2; Bernardo, B. C. et al., PHARAMCOL. THERAPEUTICS, 2010, 128(1), 191.

On the other hand, the physiological cardiac hypertrophy is mediated through the activation of tyrosine kinase receptors by growth hormone (GH) and insulin-like growth factor I (IGF-I) which culminate in triggering the phosphoinositide 3-kinase—RAC-α serine/threonine-protein kinase enzyme and Akt (PI3K—AKT) pathway. Bernardo, B. C. et al., CARDIOL. CLIN, 2010, 34(4), 515.

In physiological cardiac hypertrophy, the increase in the cardiac size is related to an equivalent growth of functional cells (e.g., cardiomyocytes) and supportive cells (such as fibroblasts). An increase in cardiomyocyte size mimics normal growth as there is normal upregulation of the contractile filaments and the ion channels which lead to an enhancement of the contractile and electrical activity of the heart.

Furthermore, physiological cardiac hypertrophy is accompanied by equivalent angiogenetic growth that provides the required increase in the blood supply to meet demand.

In contrast, pathological cardiac hypertrophy is extensive and characterized by a huge increase in the supportive cells (e.g. fibroblasts) and the collagen fibers compared to the functional normal cardiomyocytes which ultimately disturb the normal ratio of functional to nonfunctional cells. The cardiomyocytes of this type of hypertrophy also suffer of maladaptation due to the switch of fetal genes that encode weak contractile myofilaments which lead to reduced force of contraction. The number and structure of ion channels are also reduced compared to the increment in the size of the cardiomyocytes and this consequently predisposes the new enlarged heart to arrhythmias. Moreover, in pathological cardiac hypertrophy there is no parallel angiogenetic growth which might lead to ischemia of a newly hypertrophied heart.

One pathological factor associated with pathological cardiac hypertrophy is increased aortic pressure, which increases the afterload on the ventricle, reduces stroke volume by increasing end-systolic volume, and leads to a secondary increase in ventricular preload.

Other pathological conditions include ventricular systolic failure and valve defects such as aortic stenosis, and aortic regurgitation (pulmonary valve stenosis and regurgitation have similar effects on right ventricular preload).

In contrast, during induction of physiological cardiac hypertrophy an increase in volume load or stress is moderate and intermittent only during the period of exercise in comparison to conditions inducing pathological cardiac hypertrophy.

Volume overload is best correlated with physiological hypertrophy particularly if it is moderate and intermittent. Volume overload refers to the state of one of the chambers of the heart in which too large a volume of blood exists within it for it to function efficiently. Ventricular volume overload is approximately equivalent to an excessively high preload (amount of sarcomere stretch of cardiac muscle cells). It is a cause of cardiac failure, especially cardiac failure due to large progressive and persistent volume overloads. Though not exactly equivalent to the strict definition of preload, end-diastolic volume is better suited to the clinic. It is relatively straightforward to estimate the volume of a healthy, filled left ventricle by visualizing the 2D cross-section with cardiac ultrasound.

Ventricular filling and therefore preload is increased by: increased central venous pressure that can result from decreased venous compliance (e.g., caused by sympathetic activation of venous smooth muscle) or increased thoracic blood volume. The latter can be increased by either increased total blood volume or by venous return augmented by increased respiratory activity, increased skeletal muscle pump activity, or by effect of gravity (e.g., head-down tilt). Increased ventricular compliance, which results in a greater expansion of the chamber during filling at a given filling pressure. Increased atrial force of contraction resulting from sympathetic stimulation of the atria or from increased filling of the atria and therefore increased atrial contractile force through the Frank-Starling mechanism. Reduced heart rate, which increases ventricular filling time.

Pressure overload (increased after load) is associated with pathological hypertrophy. However, overlap and cross talk between these two pathways do exist. For example if volume overload becomes extensive in competitive sports, it can induce pathological cardiac hypertrophy. While, moderate and intermittent increase in afterload precipitated by resistant exercises can lead to physiological hypertrophy.

*Nigella sativa* (Ns), which is a traditional remedy in the Middle East, was found to induce cardiac hypertrophy in Wistar rats after 8 weeks of oral administration; Al-Asoom, et al., Cardiovascular Toxicology, 2014, 14(3), 243. However, the major molecular elements involved in both pathological and physiological hypertrophy pathways were not previously explored and their interrelationship to exercise and administration of *Nigella sativa* were previously unknown.

The inventors sought to new ways to induce physiological cardiac hypertrophy and reduce pathological cardiac hypertrophy. Accordingly, they investigated the biochemical and physiological effects of exercise, administration of *Nigella sativa*, and the effects of a combination of both exercise and administration of *Nigella sativa*. The methods and compositions disclosed herein may advantageously be used to treat athletic subjects at risk of pathological cardiac hypertrophy including athletes on rigorous, intensive, or prolonged exercise regimens and other subjects subjected to pressure overload, such as those with hypertension or with stenosis, such as heart valve stenosis; or those having low myocardial tolerance of ischemia-reperfusion injury.

BRIEF SUMMARY OF THE INVENTION

The foregoing paragraphs have been provided by way of general introduction, and are not intended to limit the scope of the following claims. The described embodiments, together with further advantages, will be best understood by reference to the following detailed description taken in conjunction with the accompanying drawings.

One aspect of the invention is a method for inducing or enhancing physiological cardiac hypertrophy and/or preventing or reducing the severity of pathological cardiac hypertrophy, especially in athletes subject to pathological cardiac hypertrophy due to over-exertion or over-training or to prolonged exercise regimens.

Another aspect of the invention is a method for inducing or enhancing physiological cardiac hypertrophy and/or reducing pathological cardiac hypertrophy in non-athletic individuals having or at risk of having pathological cardiac hypertrophy by administering *Nigella sativa* or an extract or component thereof.

Another aspect of the invention is a composition comprising *Nigella sativa* or an extract or component thereof in a form suitable for administration to a subject especially for prevention or treatment of pathological hypertrophy or for induction of physiological cardiac hypertrophy.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

DETAILED DESCRIPTION OF THE INVENTION

Figure 1A:
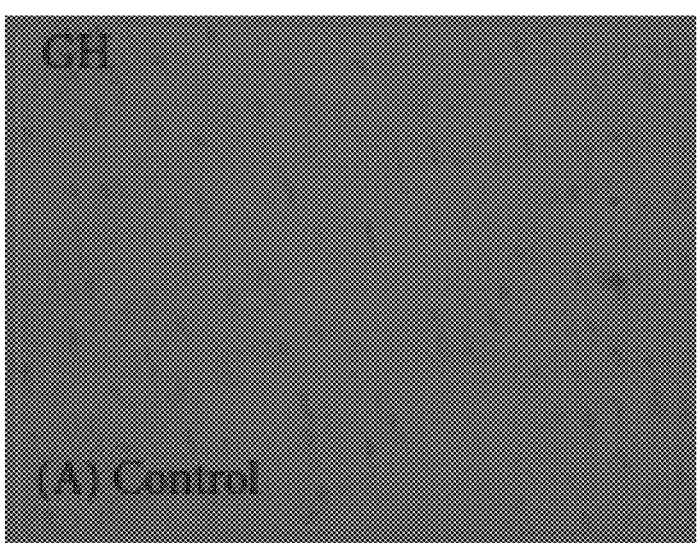
FIGS. 1A-1D. Photomicrographs of the immunohistochemical slides of the left ventricular wall stained with growth hormone (GH) obtained from Control (FIG. 1A) *Nigella sativa* fed group (FIG. 1B), exercise-trained group (FIG. 1C) and *Nigella sativa*, exercise-trained group (FIG. 1D).

As shown herein, beneficial physiological cardiac hypertrophy is induced by long-term administration of *Nigella sativa* resulting in enhanced cardiac function. The results reported below further characterize the molecular mechanisms associated with the induction of physiological cardiac hypertrophy by administration of *Nigella sativa*, by exercise, or by a combination of administration of *Nigella sativa* and exercise.

Embodiments of the invention include, but are not limited to, the following.

A method for reducing the severity of pathological cardiac hypertrophy and/or inducing physiological cardiac hypertrophy, comprising identifying a subject having, or at risk of developing, pathological cardiac hypertrophy and/or in need of physiological cardiac hypertrophy, and orally administering to said subject an amount of *Nigella sativa* for a time that reduces the severity of pathological cardiac hypertrophy and/or that increases physiological cardiac hypertrophy compared to a control subject not receiving the *Nigella sativa*. Typically, or usually, *Nigella sativa* must be administered for an extended time in order to reduce or prevent pathological cardiac hypertrophy or to induce or enhance physiological cardiac hypertrophy, for example, for a period of several weeks.

In some embodiments of this method, the subject has pressure or stress overload caused by chronic, intense, or prolonged exercise training.

In other embodiments, the subject is an athlete or other subject who has a $VO_2$ max classified as Excellent or Superior and/or has an average resting heart rate classified as Athletic or Excellent as described by Tables 1 and 2. In some alternative embodiments other types of subjects as described by Tables 1 and 2 may be treated.

In other embodiments, the subject intensely exercises at least once, twice, three-times, four-times, five-times or more per week, wherein intense exercise comprises exercising at more than 85% of the subject's maximum heart rate, wherein maximum heart rate is calculated by subtracting the subject's age from 220.

In other embodiments, the subject vigorously exercises at least once, twice, three-times, four-times, five-times or more a week, wherein vigorous exercise comprises exercising at >70 to 85% of the subject's maximum heart rate, wherein maximum heart rate is calculated by subtracting the subject's age from 220.

In still other embodiments, the subject moderately exercises at least once, twice, three-times, four-times, five-times or more a week, wherein moderate exercise comprises exercising at 50 to 70% of the subject's maximum heart rate, wherein maximum heart rate is calculated by subtracting the subject's age from 220.

Such exercise may be performed over a period of 5, 10, 15, 30, 60, 90, 120 or <120 minutes. In some cases, the exercise period is repeated over the course of a day, for example, twice, three-times, four-times or more.

In some embodiments, a subject will have a volume overload as described herein. In other embodiments, <5, 5, 10, 15, 20, 25, 30, 35, 40, 45, 50 or >50% of blood may be regurgitated from the left ventricle through the mitral valve.

Regurgitation of blood through heart valves is considered pathological, not physiological, and as leading to pathological hypertrophy and not physiological hypertrophy.

In other embodiments of this method the subject has pressure or stress overload caused by hypertension, valvular heart disease, valvular injury, injury of the cardiac muscle due to ischemia and infarction.

Current recommendations toward assessing a candidate before engagement in any competitive sport, include ECG, echocardiography, past medical history and family history of cardiac diseases. Certain signs in the ECG such as abnormal Q-T segment, T wave inversion can suggest that a candidate can develop cardiac hypertrophy when exposed to strenuous training. Other signs include those described by, and incorporated by reference to, Abibillaev, D. et al., HEART VESSELS TRANSPLANT 2020; 4; doi: 10.24969/hvt.2020.199.

A subject may be classified or selected based on their blood pressure. Normal blood pressure is below 120 (systolic in mm Hg) and below 80 (diastolic in mm Hg). Elevated blood pressure is 120-129 (systolic) and below 80

(diastolic). Stage 1 hypertension is 130-139 (systolic) and 80-89 (diastolic). Stage 2 hypertension is 140 or higher (systolic) and 90 or higher (diastolic). Hypertension correlates with risk of pathological cardiac hypertrophy.

In some embodiments, the subject has a body mass index (BMI) of 25, 30, 35, 40, 45, 50 or more with a higher body mass generally correlated with an increased risk of pathological cardiac hypertrophy.

In other embodiments, a subject's fitness or athletic characterization may be determined based on body fat, for example, athletic males and females will have a body fat of 5-10% or 16-19% respectively. Acceptable males and females will have a body fat of 15-17% or 20-24% respectively. Overweight males and females will have a body fat of 18-19% or 24-29% respectively. Obese males and females will have a body fat of 20% or more or at least 30%, respectively.

In other embodiments, blood oxygen levels may be used to characterize or select an athlete or other subject. Hyperoxemia is generally detected using ABG testing and is defined as blood oxygen levels above 120 mmHg. Normal arterial oxygen pressure (PaO2) measured using the arterial blood gas (ABG) test is approximately 75 to 100 millimeters of mercury (75-100 mmHg). When the level goes below 75 mm Hg, the condition is generally termed as hypoxemia. The most commonly used method of measuring blood oxygen levels in hospitals is a small device—resembling a clip—called a pulse oximeter. The oximeter is placed on a small, translucent part of your body like a fingertip or ear lobe where there isn't a whole lot going on. By shining a light through your skin to a sensor on the other side, the device very cleverly uses the color of your arterial blood to estimate the amount of oxygen contained within. Thus, depending on activity level or for athletes the type and duration of exercise, a subject may be classified as one whose condition is hyperoxemic, normooxemic or hypoxemic either at rest or during exercise. Some athletes will exercise for 0.25, 0.5, 1, 2, 3, 4 or more hours primarily in one of these conditions.

Subjects may also be classified or selected based on their predominant type of exercise or exertion. A shot-putter or sprinter satisfies energy requirements differently than a marathon runner. There are 3 distinct yet closely integrated processes that operate together to satisfy the energy requirements of muscle. The anaerobic energy system is divided into alactic and lactic components, referring to the processes involved in the splitting of the stored phosphagens, ATP and phosphocreatine (PCr), and the nonaerobic breakdown of carbohydrate to lactic acid through glycolysis. The aerobic energy system refers to the combustion of carbohydrates and fats in the presence of oxygen. The primary system satisfying the energy requirements of a subject or the number of hours spent exercising utilizing different energy systems may be used to classify or select a subject.

A subject or athlete may be classified or selected based on body composition, such as by muscle mass. Normal ranges for muscle mass for ages 20-39: 75-89 percent for men, 63-75.5 percent for women; ages 40-59: 73-86 percent for men, 62-73.5 percent for women; and for ages 60-79: 70-84 percent for men, 60-72.5 percent for women.

Heart ejection fraction may also be used to classify subjects. Ejection fraction is a measurement of the percentage of blood leaving the heart each time it contracts. Normal ejection fractions range from about 50-70% and borderline ejection fractions between 41 and 50%. Ejection fraction may be negatively impacted by weakness of the heart muscle or cardiomyopathy, prior heart attack that damaged the cardiac muscle, heart valve problems, or long-term uncontrolled blood pressure. Thus, a low or below normal heart ejection fraction can correlate with the presence of pathological cardiac hypertrophy or a normal heart ejection fraction with physiological cardiac hypertrophy. Ejection fractions may be measured with respect to normal controls or longitudinally in the same subject.

Ejection fractions may be measured with imaging tests including echocardiogram, cardiac catheterization, MRI, CT or a nuclear medicine scan.

In other embodiments, the subject has hypertension characterized by blood pressure of higher than 140/90.

In some embodiments, the subject is diabetic or pre-diabetic and has an A1C (percent) of 5.7% or more, a fasting plasma glucose of 100 or more, and/or an oral glucose tolerance test value of 200 or above. A subject may be diabetic (Type 1 or 2) or pre-diabetic and have an A1C (percent) of 5.7, 6.0, 6.5% or more, a fasting plasma glucose of 100, 120, 130, 140 150 or more, and/or an oral glucose tolerance test value of 200, 210, 220, 230, 240 or 250 or above. A subject may also not be diabetic or prediabetic and not meet these criteria.

In other embodiments, the subject has an elevated level of endothelin (ET-1) and/or angiotensin II receptor type 1 (AT-1) in cardiac muscle.

In other embodiments, the subject is identified has having a higher than normal plasma level of ET-1, wherein a normal level in the healthy control is 0.08±0.13 fmol/mL.

In some embodiments, the subject is identified has having a higher than normal plasma level of angiotensin, wherein a normal level in the healthy control is <5, 10, 15, 20, 25, 30, 35-40 pg/mL. In one embodiment, angiotensin II levels are measured. Too much angiotensin causes the body to retain too much fluid or to have elevated blood pressure levels not caused by other problems. High angiotensin levels can also cause the heart to grow, leading to heart failure.

In other embodiments of this method the subject is identified has having a higher than normal plasma level of ET-1, wherein a normal level in the healthy control is 0.08±0.13 fmol/mL; and/or the subject is identified has having a higher than normal plasma level of angiotensin II, wherein a normal level in the healthy control is <5, 5, 10, 15, 20, 25, 30, 34-40 pg/mL. Plasma levels of ET-1 or other compounds may serve as surrogate markers for levels of ET-1 in cardiac muscle, preferably, cardiac muscle in the left ventricle.

Although the increase in endothelin-1 can act as a mediator for pathological cardiac hypertrophy, clinically, other downstream markers are used to assess the pathological remodeling of the heart. Downstream biomarkers are described by, and incorporated by reference to Berezin, A. E., & Berezin, A. A., *Adverse Cardiac Remodelling after Acute Myocardial Infarctions Old and New Biomarkers*. DISEASE MARKERS, 2020, 1.215802. Hypertext transfer protocol secure://doi.org/1.0.1155/2020/1215802, These include elevated levels of high-specific cardiac troponins T (hs-TnT) and I (hs-TnI) in peripheral blood which can be used as diagnostic and predictive biomarkers for acute coronary syndromes and AMI. Other biomarkers include growth/differential factor-15, MMP-2, MMP-6, MMP-9, adipocytokines (apelin, chemerin, and visfatin), circulating endothelial and mononuclear progenitor cells, activated and apoptotic endothelial cell-derived microvesicles, miRNAs, and bone-related proteins.

In other embodiments, the subject is administered at least 25, 50, 100, 200, 300, 400, 500, 600, 700, 800, 900, or >1,000 mg/kg *Nigella sativa* at least three, four, five, six, or seven times a week or at least once each day for a period of at least 1, 2, 3, 4, 5, 6, 7, 8, 9, 10 or more weeks.

In some embodiments, the *Nigella sativa* is administered no more than 0.25, 0.5, 0.75, 1, 1.25, 1.5, 1.75 or 2 hours before moderate, vigorous, or intense exercise; or wherein the *Nigella sativa* is administered no more than 0.25, 0.5, 0.75, 1, 1.25, 1.5, 1.75 or 2 hours after moderate, vigorous, or intense exercise.

In some embodiments, this method comprises administering other active compounds, such as a method further comprising administering an AKT antagonist or an Erk1/2 antagonist; or a methods further comprising administering an angiotensin-II receptor antagonist and/or administering an endothelin-1 receptor antagonist.

Another aspect of the invention is composition comprising *Nigella sativa* or an extract thereof and at least one angiotensin-II receptor antagonist, endothelin-1 receptor agonist, or Erk-1/2 inhibitor. Typically, the composition is edible or ingestible and may be in the various forms described herein.

Several tests are available to diagnose physiological or pathological hypertrophy (cardiomyopathy) or rule it out including: Echocardiogram. An echocardiogram is commonly used to diagnose hypertrophic cardiomyopathy. This test uses sound waves (ultrasound) to see if the heart's muscle is abnormally thick. It also shows how well the heart's chambers and valves are pumping blood. Sometimes, an echocardiogram is done during exercise, usually on a treadmill. This is called an exercise stress test. Treadmill stress tests are commonly used to diagnose people with hypertrophic cardiomyopathy. Electrocardiogram (ECG or EKG). Sensors (electrodes) attached to adhesive pads are placed on the chest and sometimes legs. They measure electrical signals from the heart. An ECG can show abnormal heart rhythms and signs of heart thickening. In some cases, a portable ECG, called a Holter monitor, is needed. This device records the heart's activity continuously over one to two days. Cardiac MRI. A cardiac MRI uses powerful magnets and radio waves to create images of the heart. It gives a doctor information about a subject's heart muscle and shows how the heart and heart valves work. This test is often done with an echocardiogram.

Pathological and physiological cardiac hypertrophies are caused by different stimuli, functionally distinguishable, and are associated with distinct structural and molecular phenotypes, see the Table A below. A subject may be screened or selected using one or more of these criteria.

|  | Pathological Hypertrophy | Physiological Hypertrophy |
| --- | --- | --- |
| Stimuli | Pressure load in a disease setting (e.g. hypertension, aortic coarction) or volume load (e.g. valvular disease) Cardiomyopathy (familial, viral, toxic, metabolic) Increased myocyte volume | Regular physical activity or chronic exercise training Volume load (e.g. running, walking, swimming) Pressure load (e.g. strength training: weight lifting) Increased myocyte volume |
| Cardiac morphology | Formation of new sarcomeres Interstitial fibrosis Myocyte necrosis and apoptosis | Formation of new sarcomeres |

-continued

| | Pathological Hypertrophy | Physiological Hypertrophy |
|---|---|---|
| Fetal gene expression | Usually upregulated | Relatively normal |
| Cardiac function | Depressed over time | Normal or enhanced |
| Completely reversible | Not usually | Usually |
| Association with heart failure and increased mortality | Yes | No |

Subjects having pathological cardiac hypertrophy due to hypertension, valvular heart disease or injury or other diseases affecting cardiac muscle, known as cardiomyopathies, are the leading cause of death in developed countries. The most common condition is coronary artery disease, in which the blood supply to the heart is reduced. The coronary arteries become narrowed by the formation of atherosclerotic plaques. If these narrowings become severe enough to partially restrict blood flow, the syndrome of angina pectoris may occur. This typically causes chest pain during exertion that is relieved by rest. If a coronary artery suddenly becomes very narrowed or completely blocked, interrupting or severely reducing blood flow through the vessel, a myocardial infarction.

Diseases affecting cardiac muscle, known as cardiomyopathies, are the leading cause of death in developed countries. The most common condition is coronary artery disease, in which the blood supply to the heart is reduced. The coronary arteries become narrowed by the formation of atherosclerotic plaques. If these narrowings become severe enough to partially restrict blood flow, the syndrome of angina pectoris may occur. This typically causes chest pain during exertion that is relieved by rest. If a coronary artery suddenly becomes very narrowed or completely blocked, interrupting or severely reducing blood flow through the vessel, a myocardial infarction or heart attack occurs. If the blockage is not relieved promptly by medication, percutaneous coronary intervention, or surgery, then a heart muscle region may become permanently scarred and damaged. A specific cardiomyopathy, can cause heart muscle to become abnormally thick (hypertrophic cardiomyopathy), abnormally large (dilated cardiomyopathy), or abnormally stiff (restrictive cardiomyopathy). Some of these conditions are caused by genetic mutations and can be inherited. Heart muscle can also become damaged despite a normal blood supply. The heart muscle may become inflamed in a condition called myocarditis, most commonly caused by a viral infection but sometimes caused by the body's own immune system. Heart muscle can also be damaged by drugs such as alcohol, long standing high blood pressure or hypertension, or persistent abnormal heart racing. Many of these conditions, if severe enough, can damage the heart so much that the pumping function of the heart is reduced. If the heart is no longer able to pump enough blood to meet the body's needs, this is described as heart failure.

Significant damage to cardiac muscle cells is referred to as myocytolysis which is considered a type of cellular necrosis defined as either coagulative or colliquative. If the blockage is not relieved promptly by medication, percutaneous coronary intervention, or surgery, then a heart muscle region may become permanently scarred and damaged. A specific cardiomyopathy, can cause heart muscle to become abnormally thick (hypertrophic cardiomyopathy), abnormally large (dilated cardiomyopathy), or abnormally stiff (restrictive cardiomyopathy). Some of these conditions are caused by genetic mutations and can be inherited.

Heart muscle can also become damaged despite a normal blood supply. The heart muscle may become inflamed in a condition called myocarditis, most commonly caused by a viral infection but sometimes caused by the body's own immune system. Heart muscle can also be damaged by drugs such as alcohol, long standing high blood pressure or hypertension, or persistent abnormal heart racing. Many of these conditions, if severe enough, can damage the heart so much that the pumping function of the heart is reduced. If the heart is no longer able to pump enough blood to meet the body's needs, this is described as heart failure. Significant damage to cardiac muscle cells is referred to as myocytolysis which is considered a type of cellular necrosis defined as either coagulative or colliquative.

The methods described herein may be used to reduce the severity of the above-mentioned diseases or conditions.

In other embodiments, the methods as disclosed herein may be used to treat subjects for ischemia-reperfusion injury or its symptoms or sequela. This type of injury results when ischemia due to inadequate oxygen supply is followed by successful reperfusion initiating a wide and complex array of inflammatory responses that may both aggravate local injury as well as induce impairment of remote organ function.

These related conditions may benefit from administration of *Nigella sativa* which is shown herein to interfere with the pathological pathway resulting in pathological cardiac hypertrophy.

Routes of administration. *Nigella sativa* compositions may be administered by a variety of routes and forms, but are preferably administered orally or in a form in which active components can come into contact with the circulatory system and heart. The methods of administering *Nigella sativa* or its extracts or compositions containing them disclosed herein may comprise administering a silver or titanium oxide nanoparticle composition or composition intravenously, intramuscularly, topically, intradermally, intramucosally, subcutaneously, sublingually, orally, intravaginally, intracavernously, intraocularly, intranasally, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, transmucosally, or transdermally.

Carriers/Excipients. The term carrier encompasses any excipient, binder, diluent, filler, salt, buffer, solubilizer, lipid, stabilizer, or other material well known in the art for use in pharmaceutical formulations, for example, for intravenous administration a carrier may be sodium chloride 0.9% or mixtures of normal saline with glucose or mannose. The choice of a carrier for use in a composition will depend upon the intended route of administration for the composition. The preparation of pharmaceutically acceptable carriers and formulations containing these materials is described in, e.g., *Remington's Pharmaceutical Sciences,* 21st Edition, ed. University of the Sciences in Philadelphia, Lippincott, Williams & Wilkins, Philadelphia Pa., 2005, which is incorporated herein by reference in its entirety.

Formulations for administration. For therapeutic purposes, formulations for parenteral administration of compositions comprising *Nigella sativa* or its extracts can be in the form of aqueous or non-aqueous isotonic sterile injection solutions or suspensions. The term parenteral, as used herein, includes intravenous, intravesical, intraperitoneal, subcutaneous, intramuscular, intralesional, intracranial, intrapulmonal, intracardial, intrasternal, and sublingual injections or infusion techniques.

Oral administration. Solid preparations for oral administration may include a tablet, a pill, a powder, a granule, a capsule, and the like. These solid preparations may be prepared by mixing at least one excipient, such as starch, calcium carbonate, sucrose, lactose, or gelatin, with nanoparticle as disclosed herein. In addition to such a simple excipient, lubricants, such as magnesium stearate and talc, may be used. Liquid preparations containing *Nigella sativa* or its extracts for oral administration correspond to a suspension, a liquid for internal use, oil, syrup, and the like, and may include several types of excipient, for example, a wetting agent, a sweetener, an aroma, a preservative, and the like, in addition to simple diluents that are frequently used, such as water and liquid paraffin.

Parenteral administration. Injectable preparations, for example, sterile injectable aqueous or oleaginous suspensions containing *Nigella sativa* or typically its extracts or isolated active components can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or diglycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Respiratory system administration. Administration to the respiratory system may be accomplished using a drug delivery device such as a nebulizer to administer a nanoparticle composition as disclosed herein, in an inhalable form. Nebulizers include soft mist inhalers, jet nebulizers, ultrasonic wave nebulizers, and nebulizers using vibrating mesh technology. A metered-dosage inhaler is another drug delivery device that delivers a selected or metered amount of a medication, such as the nanoparticle compositions disclosed herein. Typically, this device produces and releases an aerosol of micrometer-sized particles that are inhaled. The aerosol will comprising *Nigella sativa* or its extracts component thereof as disclosed herein and may contain excipients or carriers.

Thus, preferably, particles comprising an extract are sized so as to provide a uniform dosage or so they are absorbed in a particular part of the respiratory system. In some cases, the particles may be a dry powder in others as a mist or in a semiliquid form. Metered-dose inhalers and their various components, propellants, excipients and other elements are described by and incorporated by reference to hypertext transfer protocol secure://en.wikipedia.org/wiki/Metered-dose inhaler. An inhalable composition may be formulated in the form of a hydrofluoroalkane inhaler or HFA (metered dose inhaler or MDI), dry powder inhaler (DPI), or as a nebulizer solution.

Dose. The dose of *Nigella sativa* or its extracts as disclosed herein with respect to the human or animal body may vary depending on patient's age, body weight, and gender, the form of administration, state of health, and severity of disease. The dose may be generally 0.01-100 mg/kg/day, preferably 0.1-20 mg/kg/day, and more preferably 5-10 mg/kg/day. The composition may also be divisionally administered at predetermined intervals according to converted or adjusted based on body surface area, e.g., to $mg/m^2$. Such adjustments or conversions may be calculated using formulas known in the art; see DuBois D & DuBois E F. A formula to estimate the approximate surface area if height and weight be known. Arch Intern Medicine. 1916; 17:863-71; and Wang Y, Moss J, Thisted R. *Predictors of body surface area*. J Clin Anesth. 1992; 4(1):4-10, both of which are incorporated by reference.

In some embodiments of this method, further active agents are co-administered in conjunction with *Nigella sativa* and/or an exercise regimen. Thus include antagonists, an angiotensin-II receptor antagonist, endothelin-1 receptor antagonist, an Erk1/2 antagonist, at least one agent that increases IGF-1 or growth hormone (GH) levels, an agent that produces or releases nitric oxide (NO), at least one anti-oxidant, at least one agent that increases mitochondrial biogenesis or mitochondrial density; at least one agent that maintains or increases mitochondrial respiration when administered with the *Nigella sativa*; and/or administering at least one agent that increases mitochondrial apoptosis.

The term antioxidant is used to denote the substances which inhibit oxidation or suppress reactions promoted by oxygen or peroxides. Antioxidants, especially lipid-soluble antioxidants, can be absorbed into the cellular membrane to neutralize oxygen radicals and thereby protect the membrane or protein components of a composition for oxidation. The compositions of the present application may comprise one or more antioxidants or vitamin co-factors, selected from, but not limited to ascorbic acid (vitamin C), ascorbyl palmitate, glutathione, lipoic acid, uric acid, vitamin A, carotenes such as alpha-carotene, beta-carotene, astaxanthin, canthaxantin, cryptoxanthin, lutein, lycopene, and zeaxanthin, alpha-tocopherol (vitamin E) and other tocopherols, tocofersolan, ubiquinol, butylated hydroxyanisole, butylated hydroxytoluene, sodium benzoate, propyl gallate (PG, E310), and tertiary-butylhydroquinone, flavonoids, flavones including apigenin, luteolin, and tangeritin; flavonols including isorhamnetin, kaempferol, myricetin, proanthocyanidins, quercetin and rutin; flavanones including eriodictyol, hesperetin, naringenin; flavanols and their polymers including catechin, gallocatechin and their gallate esters, epicatechin, epigallocatechin and their gallate esters, theaflavin and its gallate esters, thearubigins; isoflavone phytoestrogens including daidzein, genistein, and glycitein; stilbenoids including resveratrol and pterostilbene; anthocyanins including cyaniding, dephinidin, malvidin, pealgonidin, peonidin, and petrunidin; phenolic acids and their esters including chicoric acid, chlorogenic acid, cinnamic acid, ellagic acid, allagitannins, gallic acid, gallotannins, rosmarinic acid, and salicylic acid; and other nonflavonoic phenols including curcumin, favonolignans such as silymarin, xanthones such as mangosteen, and eugenol. Other antioxidants include propyl gallate (PG, E310), tertiary butylhydroquinone (TBHQ), butylated hydroxyanisole (BHA, E320) and butylated hydroxytoluene. Cofactors such as CoQ10, manganese, or iodide may be included in a composition as disclosed herein. The amounts of antioxidants or cofactors may range from about 0.001, 0.002, 0.005, 0.01, 0.02, 0.05, 0.1, 0.2, 0.5, 1.0, 2.0, 5.0 to about 10%, of the total weight of the composition.

Mitochondrial-active agents include compounds or extracts that activate, feed, or induce replication of mitochondria or which destroy damaged mitochondria. Representative mitochondrial nutrients include, but are not limited to, resveratrol, grape seed extract, quercetin, pterostilbene, resveratrol, fisetin, black tea (theaflavins), ubiquinol CoQ10, R-lipoic acid, L-camitine, acetyl-L-carnitine, pyrroloquinoline quinone (PQQ), tocopherols, tocotrienols (mixed), Vitamin D3 (cholecalciferol), green tea extract (98% polyphenols, 45% epigallocatechin gallate (EGCG)), dehydroepiandrosterone (DHEA), vitamin B complexes (e.g., comprising B1, B2, B5, B6, B7 and/or B12), magnesium biglycinate, magnesium, creatine, curcumins, glucose and D-ribose. One or more mitochondrial-active agents may be incorporated into a *Nigella sativa* composition or extract. In this aspect, a synergistic amount of the mitochondrial nutrients may be combined such that the therapeutic effects of the mitochondrial nutrients when administered in combination is greater than their effect when administered alone. Representatively, three formulations including different combinations of the mitochondrial nutrients are shown herein to rescue mitochondrial dysfunction. Additionally, the combinations of mitochondrial nutrients are shown to relieve one or more disorders associated with the aging process. The amounts of mitochondrial-active agents may range from about 0.001, 0.002, 0.005, 0.01, 0.02, 0.05, 0.1, 0.2, 0.5, 1.0, 2.0, 5.0 to about 10%, of the total weight of the composition.

Another aspect of the invention is a composition comprising *Nigella sativa* or an extract thereof in combination with one or more angiotensin-II receptor antagonists, endothelin-1 receptor antagonists or Erk-1/2 inhibitors and a method of using such a composition to additively or synergistically induce physiological cardiac hypertrophy and/or reduce pathological cardiac hypertrophy compared to an untreated control subject. In some embodiments, a *Nigella sativa* composition may contain one or more enhancers of GH or IGF-1 (including GH, somatropin, GHRH, IGF-1/ Increlex) that enhance the effects of the GH-IGF I-PI3KAkt pathway on producing physiological cardiac hypertrophy. Administration of glutamine, creatine, ornithine, melatonin, L-dopa and glycine has been shown to increase GH levels. The amounts of these antagonists, inhibitors or enhancers described above may be selected by one skilled in the art. In some embodiments the form from about 0.001, 0.002, 0.005, 0.01, 0.02, 0.05, 0.1, 0.2, 0.5, 1.0, 2.0, 5.0 to about 10%, of the total weight of the composition containing *Nigella sativa* or its extract.

*Nigella sativa* and its extracts. *Nigella sativa* may be ingested in various forms, such as raw, fruit, or as a food ingredient. Preferably, it is ingested as a seed or a ground seed or as leaves, stems or roots, or as a fraction or an extract, such as *Nigella sativa* oil or as an ethanol or supercritical carbon dioxide extract of its seeds. An aqueous-alcohol extract preferably contains at least 30, 40, 50, 60, 70, 80, 90 or >90 vol. % alcohol, such as methanol, ethanol, or propanol or acetone. Extraction may be performed at a temperature ranging from <0, 0, 10, 20, 30, 40, 50, 60, 70, 80, 90 or 100° C. or at a pH ranging from <3, 3, 4, 5, 6, 7, 8, 9, or >9. The extracted components may be dehydrated, lyophilized or powdered prior to reconstitution or ingestion. In one embodiment, the insoluble fraction of *Nigella sativa* after extraction of soluble components as described above is used in the methods disclosed herein.

In some embodiments, *Nigella sativa* seeds, ground seeds or other plant parts may be extracted using super-critical $CO_2$, vegetable oils or other oily solvents, or other solvents that remove hydrophilic or hydrophobic components of *Nigella sativa*.

In one embodiment, freshly ground *Nigella sativa* seeds are incorporated into a composition as disclosed herein or ingested, such as those harvested from the Qassim area in Saudi Arabia. *Nigella sativa* or its extracts may be incorporated into a food or beverage, such as a sports beverage or sports recovery beverage which may contain other components disclosed herein. *Nigella sativa* seeds, ground seeds or desiccated extracts may be incorporated into tablets or capsules and/or may be formulated in a timed-release form or sustained release form that upon ingestion is digested over, or for extracts or soluble components, are released over, a period of 0.5, 1, 2, 3, or 4 hours. *Nigella sativa* compositions may also be prepared in pulse release form for release within a period of 0.25, 0.5 or 1 hour or in a delayed release form for release in the stomach or, alternatively in the intestines. *Nigella sativa* compositions may be formulated for sublingual or buccal release of soluble components. Modified-release compositions may be formulated by methods known in the art include, but not limited to, microencapsulation, in a diffusion system such as a reservoir device or as dispersed in a matrix such as a gelling agent, in an osmotic controlled-release delivery system such as a rigid tablet with a semi-permeable membrane covering, in combination with an ion-exchange resin, as part of a floating system, as part of a bioadhesive system, or as part of a matrix system, for example, in hydrophobic matrices, lipid matrices, hydrophilic matrices, biodegradable matrices, and mineral matrices.

Modified-release systems such as those described above and their components and structures are incorporated by reference to Khalane, L. et al., *Sustained Release Drug Delivery System: A Concise Review*. PHARMATUTOR: PHARMACY INFOPEDIA. 2012 (last accessed Jun. 23, 2021; Reference Id: PHARMATUTOR-ART-1433); or Manish, J. et al., *Sustained Release Matrix Type Drug Delivery System: A Review*. JOURNAL OF DRUG DELIVERY & THERAPEUTICS, 2012, 2(6), 142; or to hypertext transfer protocol secure://en.wikipedia.org/wiki/Modified-release_dosage (last accessed Jun. 23, 2021).

Modes of administration of the compositions disclosed herein include intravenously, intramuscularly, topically (e.g. on or into a wound or lesion), intradermally, into or over a wound, intramucosally, subcutaneously, sublingually, orally, intravaginally, intracavernously, intraocularly, intranasally, intrarectally, gastrointestinally, intraductally, intrathecally, subdurally, extradurally, intraventricular, intrapulmonary, into an abscess, intra articularly, into a bursa, subpericardially, into an axilla, intrauterine, into the pleural space, intraperitoneally, transmucosally, or transdermally. A preferred mode of administration is oral.

Angiotensin II is a naturally occurring peptide hormone of the renin-angiotensin-aldosterone-system (RAAS) that has the capacity to cause vasoconstriction and an increase in blood pressure in the human body. In the RAAS, juxtaglomerular cells of the renal afferent arteriole synthesize the proteolytic enzyme renin.

The angiotensin II receptors, (ATR1) and (ATR2), are a class of G protein-coupled receptors with angiotensin II as their ligands. They are important in the renin-angiotensin system: they are responsible for the signal transduction of the vasoconstriction stimulus of the main effector hormone, angiotensin II.

Angiotensin II receptor blockers (ARBs) work by preventing angiotensin II from binding to angiotensin II receptors on the muscles surrounding blood vessels so blood vessels enlarge (dilate) and blood pressure is reduced. Calcium channel blockers (CCBs) are used to treat high blood pressure, angina (chest pain), and abnormal heart rhythms.

These include, but are not limited to, Azilsartan, candesartan, eprosartan, irbesartan, and losartan.

Endothelin 1 (ET-1) is a potent vasoconstrictor that in humans is encoded by the EDN1 gene and produced by vascular endothelial cells. The protein encoded by this gene is proteolytically processed to release a secreted peptide termed endothelin 1. Endothelin 1 is one of three isoforms of human endothelin.

An endothelin receptor antagonist (ERA) is a drug that blocks endothelin receptors. Three main kinds of ERAs exist: (i) selective $ET_A$ receptor antagonists (e.g., sitaxentan, ambrisentan, atrasentan, BQ-123, zibotentan), which affect endothelin A receptors; (ii) dual antagonists (e.g., bosentan, macitentan, tezosentan), which affect both endothelin A and B receptors; and (iii) selective $ET_B$ receptor antagonists (e.g., BQ-788 and A192621) which affect endothelin B receptors are used in research but have not yet reached the clinical trial stage. Sitaxentan, ambrisentan and bosentan are mainly used for the treatment of pulmonary arterial hypertension, while atrasentan is an experimental anti-cancer drug. Edonentan is an endothelin receptor antagonist drug.

Akt (Protein kinase B, PKB) is a serine/threonine kinase that plays a key in regulating cell survival, angiogenesis and tumor formation. Akt is a downstream mediator of the PI 3-K pathway, which results in the recruitment of Akt to the plasma membrane.

ERK1/2 belong to a family of conserved serine/threonine protein kinases known as mitogen-activated protein kinases (MAPKs) that are involved in many cellular programs such as proliferation, differentiation, motility, and survival. Erk-1/2 antagonists or inhibitors include ERK1/2 inhibitor LY3214996. LY3214996 inhibits both ERK 1 and 2, thereby preventing the activation of mitogen-activated protein kinase (MAPK)/ERK-mediated signal transduction pathways. Other inhibitors include Ulixertinib, MK-8353, and GDC-0994 which are orally effective, potent, and specific inhibitors of ERK1/2.

G-protein-coupled receptor (GPCR) pathway. Pathological hypertrophy is mediated through the G-protein-coupled receptor (GPCR) pathway. The GPCR main precursors are angiotensin-II, endothelin-1, and catecholamine. The intracellular cascades involve multiple mitogen-activated protein kinase MAPK enzymes such as Erk1/2; Bernardo, B. C. et al., PHARAMCOL. THERAPEUTICS, 2010, 128(1), 191. Strenuous exercise can switch on this pathological pathway through G-protein coupled receptors and trigger maladaptations in the cardiac muscle such as increased fibrosis, reduced functional myocytes to other non-functional cell ratios, and deleterious changes in the distribution of electrolyte channels that can lead to arrythmogenic consequences. This pathway can be triggered by prolonged duration and extent of pressure or volume load on the heart. In exercise training the volume or pressure overload is intermittent while in pathological insults such as hypertension, it is persistent. Volume or pressure overload also depends on exercise intensity. Thus mild or moderate exercise will not trigger this pathway while very high intensity exercise and long duration exercise, such as in athletes running a marathon, the exercise induced pressure and volume overloads mimic those in pathological conditions and initiate GPOCR pathways.

GH-IGF I-PI3KAkt pathway. Physiological cardiac hypertrophy is mediated via the activation of tyrosine kinase receptors by growth hormone (GH) or its analogs and insulin-like growth factor I (IGF-I) that culminates in triggering the phosphoinositide 3-kinase—RAC-α serine/threonine-protein kinase enzyme and Akt (PI3K—AKT); Bernardo, B. C. et al., CARDIOL. CLIN, 2010, 34(4), 515. Exercise training is considered to induce physiological cardiac hypertrophy through activation of IGF-1—Phosphinisitol-3 phosphokinase pathway, and this pathway is associated with enlargement of the cardiomyocyte and enhancement of its function.

The terms "treatment" and "treating" as used herein refer to both prophylaxis of subjects not manifesting specific symptoms of pathological cardiac hypertrophy, for example, a subject at risk of pathological cardiac hypertrophy due to a prolonged or intense exercise regiment, as well as subjects diagnosed with or experiencing such symptoms. Such symptoms of pathological cardiac hypertrophy include, but are not limited to, chest pain with exertion, shortness of breath, heart murmur, palpitations, and fainting after exertion. Diagnosis of this condition may include echocardiogram, electrocardiogram, magnetic resonance imaging of the heart, stress test (monitoring blood pressure and heart rhythm while walking on a treadmill), and cardiac cauterization to X-ray image blood vessels.

In some instances treatment will prevent development of pathological cardiac hypertrophy and in other cases treatment will reduce the severity of pathological cardiac hypertrophy, its symptoms, or biochemical indicia. In other instances a treatment will induce or enhance physiological cardiac hypertrophy.

Volume overload refers to the state of one of the chambers of the heart in which too large a volume of blood exists within it for it to function efficiently. Ventricular volume overload is approximately equivalent to an excessively high preload. It is a cause of cardiac failure; Costanzo, L. S. (2007). Physiology. Hagerstown, MD: Lippincott Williams & Wilkins. pp. 81. ISBN 978-0-7817-7311-9.

$VO_2$ max (also maximal oxygen consumption, maximal oxygen uptake or maximal aerobic capacity) is the maximum rate of oxygen consumption measured during incremental exercise; that is, exercise of increasing intensity. The name is derived from three abbreviations: "V" for volume (the dot appears over the V to indicate "per unit of time"), "$O_2$" for oxygen, and "max" for maximum.

The measurement of $VO_2$ max in the laboratory provides a quantitative value of endurance fitness for comparison of individual training effects and between people in endurance training. Maximal oxygen consumption reflects cardiorespiratory fitness and endurance capacity in exercise performance. Elite athletes, such as competitive distance runners, racing cyclists or Olympic cross-country skiers, can achieve $VO_2$ max values exceeding 80 mL/(kg·min), while some endurance animals, such as Alaskan huskies, have $VO_2$ max values exceeding 200 mL/(kg·min).

The average sedentary male will achieve a $VO_2$ max of approximately 35 to 40 mL/kg/min. The average sedentary female will score a $VO_2$ max of between 27 and 30 mL/kg/min.

Average resting heart rate. A normal resting heart rate for adults ranges from 60 to 100 beats per minute. Generally, a lower heart rate at rest implies more efficient heart function and better cardiovascular fitness. For example, a well-trained athlete might have a normal resting heart rate closer to 40 beats per minute.

As used herein, the term athlete refers to a subject who meets athletic criteria such as average heart rate or $VO_2$ max described in Tables 1 and 2, other criteria disclosed herein, or otherwise is subject to prolonged or intense periods of exertion which can induce or aggravate pathological cardiac hypertrophy.

Physical status of subjects. The physical status of a subject may be evaluated and classified by a physician or other sports professions. Among other values, a subject may be classified by age-normalized $VO_2$ or resting heart rate as shown by the charts below.

TABLE 1A

| | | | VO2 Max Norms for Men | | | |
|---|---|---|---|---|---|---|
| Age | Very Poor | Poor | Fair | Good | Excellent | Superior—Men |
| 13-19 | Under 35.0 | 35.0-38.3 | 38.4-45.1 | 45.2-50.9 | 51.0-55.9 | Over 55.9 |
| 20-29 | Under 33.0 | 33.0-36.4 | 36.5-42.4 | 42.5-46.4 | 46.5-52.4 | Over 52.4 |
| 30-39 | Under 31.5 | 31.5-35.4 | 35.5-40.9 | 41.0-44.9 | 45.0-49.4 | Over 49.4 |
| 40-49 | Under 30.2 | 30.2-33.5 | 33.6-38.9 | 39.0-43.7 | 43.8-48.0 | Over 48.0 |
| 50-59 | Under 26.1 | 26.1-30.9 | 31.0-35.7 | 35.8-40.9 | 41.0-45.3 | Over 45.3 |
| 60+ | Under 20.5 | 20.5-26.0 | 26.1-32.2 | 32.3-36.4 | 36.5-44.2 | Over 44.2 |

TABLE 1B

| | | | VO2 Max Norms for Women | | | |
|---|---|---|---|---|---|---|
| Age | Very Poor | Poor | Fair | Good | Excellent | Superior—Women |
| 13-19 | Under 25.0 | 25.0-30.9 | 31.0-34.9 | 35.0-38.9 | 39.0-41.9 | Over 41.9 |
| 20-29 | Under 23.6 | 23.6-28.9 | 29.0-32.9 | 33.0-36.9 | 37.0-41.0 | Over 41.0 |
| 30-39 | Under 22.8 | 22.8-26.9 | 27.0-31.4 | 31.5-35.6 | 35.7-40.0 | Over 40.0 |
| 40-49 | Under 21.0 | 21.0-24.4 | 24.5-28.9 | 29.0-32.8 | 32.9-36.9 | Over 36.9 |
| 50-59 | Under 20.2 | 20.2-22.7 | 22.8-26.9 | 27.0-31.4 | 31.5-35.7 | Over 35.7 |
| 60+ | Under 17.5 | 17.5-20.1 | 20.2-24.4 | 24.5-30.2 | 30.3-31.4 | Over 31.4 |

TABLE 2A

Average resting heart rate for men by age.
Men

| Age 18-25 | Athletic: 49-55 | Excellent: 56-61 | Good: 61-65 | Average: 70-73 | Poor: Over 82 |
|---|---|---|---|---|---|
| Age 26-35 | Athletic: 49-54 | Excellent: 55-61 | Good: 62-65 | Average: 71-74 | Poor: Over 82 |
| Age 36-45 | Athletic: 50-56 | Excellent: 57-62 | Good: 63-66 | Average: 71-75 | Poor: Over 83 |
| Age 46-55 | Athletic: 50-57 | Excellent: 58-63 | Good: 64-67 | Average: 72-76 | Poor: Over 84 |
| Age 56-65 | Athletic: 51-56 | Excellent: 57-61 | Good: 62-67 | Average: 72-75 | Poor: Over 82 |
| Over Age 65 | Athletic: 50-55 | Excellent: 56-61 | Good: 62-65 | Average: 70-73 | Poor: Over 80 |

TABLE 2B

Average resting heart rate for women by age.
Women

| Age 18-25 | Athletic: 54-60 | Excellent: 61-65 | Good: 66-69 | Average: 74-78 | Poor: Over 85 |
|---|---|---|---|---|---|
| Age 26-35 | Athletic: 54-59 | Excellent: 60-64 | Good: 65-68 | Average: 73-76 | Poor: Over 83 |
| Age 36-45 | Athletic: 54-59 | Excellent: 60-64 | Good: 65-69 | Average: 74-78 | Poor: Over 85 |
| Age 46-55: | Athletic: 54-60 | Excellent: 61-65 | Good: 66-69 | Average: 74-77 | Poor: Over 84 |
| Age 56-65 | Athletic: 54-59 | Excellent: 60-64 | Good: 65-68 | Average: 74-77 | Poor: Over 84 |
| Over Age 65 | Athletic: 54-59 | Excellent: 60-64 | Good: 65-68 | Average: 73-76 | Poor: Over 84 |

Subjects may also be classified or selected based on their resting levels of angiotensin-II, endothelin-1 or catecholamine which may register increases of 10, 20, 30, 40, 50, 60, 70, 80, 90, 100 or >100% compared to an average age- and sex-matched subject.

Other athletic parameters. In some embodiments, parameters other than, or in addition to $VO_2$ max or average heart rate may be used to classify the physical status of athletic or non-athletic subjects or select a subject for treatment with *Nigella sativa*. These include, but are not limited to ratio of fast to slow twitch muscle fibers ranging from 20:80 30:70, 40:60, 50:50, 60:40, 70:30, or 80:20; blood lactate levels at rest/after moderate exercise or after heavy exertion ranging from 1, 2, 5, 10, 15 to 20 mmol/L, for example, at a $VO_2$ of 75, 80, 85-90% or at a $VO_2$ below or above this range; age ranging from <10, 10, 20, 30, 40, 50, 60, 70, 80, 90 or >90 years of age; maximum heart rate, whether a subject trains or exercises within a range of 50, 60, 70, 80-85% of maximum heart rate; and whether a subject's exercise is predominantly phosphogenic, aerobic, or anaerobic.

EXAMPLES

A series of experiments were conducted to determine the effects of supplementation with *Nigella sativa* on cardiac hypertrophy. Briefly, as explained in more detail in the Examples below, twenty adult Wistar male rats were divided into control (C), *Nigella sativa*-fed (N.s.), exercise-trained (Ex.), and *Nigella sativa*-fed exercise-trained (N.s.Ex.) groups. Groups fed with *Nigella sativa* were orally administered 800 mg/kg of *Nigella sativa*.

Ex. rats were trained on a treadmill with speed 18 m/min and grade 32° for two hours daily, and the N.s. Ex. group underwent both interventions.

After 8 weeks, immunohistochemical slides of the left ventricles were prepared using rat growth hormone (GH), insulin-like growth factor I (IGF-I), angiotensin-II receptors 1 (AT-I), endothelin-I (ET-1), Akt-1, and Erk-1.

Briefly, cardiomyocyte diameter, number of nuclei, GH, and Akt were significantly higher in N.s., Ex., and N.s.Ex groups compared with the controls. IGF-I, AT-1, and ET-1 were significantly higher than controls only in Ex. rats. Erk-1 was lower in N.s., Ex., and N.s.Ex. compared with the controls.

These results are consistent with *N. sativa*-induced cardiac hypertrophy being mediated by the GH-IGF I-PI3P-Akt pathway. Supplementation with *Nigella sativa* in exercising subjects can block the upregulation of AT-I and ET-1. Cardiac hypertrophy induced by a combination of exercise with ingestion *Nigella sativa* can provide a superior model of physiological cardiac hypertrophy and such a regimen may be used as a prophylactic therapy for athletes who are engaged in vigorous exercise activity.

Materials and Methods. This experimental work was approved by the Institutional Ethical Committee of Imam Abdulrahman Bin Faisal University, Dammam, Saudi Arabia with IRB number 2020-01-263. The minimal required number of adult healthy rats (200-300 gram in weight) was obtained from the animal house of Imam Abdulrahman Bin Faisal University. Each 5 rats were assigned for one of the following groups: control, *Nigella sativa*-fed (N.s.), exercise-trained (Ex.), and Ns-fed exercise-trained (N.s.Ex.). The rats were placed in individual labeled cages. The environment was controlled with adequate ventilation and illumination and normal light cycle (12 light/12 dark); ad libitum access to normal laboratory chow and tap water was ensured; Chen, H. I., et al., DEVELOPMENT, 2014, 141(23): 4500.

The N.s. rats received daily dose of 800 mg/kg of body weight in the form of oral solution of freshly ground N.s. for eight weeks. Details related to the preparation of the dose and the feeding technique are described by, and incorporated by reference to, Al Asoom, et al., BMC COMPLEMENTARY AND ALTERNATIVE MED, 2017, 17(1), 308.

The black seeds (N.s.) used in this study were harvested from the Qassim area in the central province of Saudi Arabia. The constituents of this type of black seeds were reported by, and incorporated by reference to, Al-Jassir, et al., FOOD CHEM. 1992, 45(4), 239. The control rats were fed with an equivalent volume of water. As described therein, proximate analysis of black cumin seeds showed a composition of 20.85% protein, 38.20% fat, 4.64% moisture, 4.37% ash, 7.94% crude fiber and 31.94% total carbohydrates. Potassium, phosphorus, sodium and iron were the predominant elements present. Zinc, calcium, magnesium, manganese and copper were found at lower levels. However, lead, cadmium and arsenic were not detected in the seeds. Linoleic and oleic acids were the major unsaturated fatty acids while palmitic acid was the main saturated one. Glutamic acid, arginine and aspartic acid were the main amino acids present while cysteine and methionine were the minor amino acids. In other embodiments of the methods and compositions disclosed herein, *Nigella sativa* seeds from other sources may be used. In some embodiments, these seeds will vary in composition from the by ±1, 2, 5, 10 or 15% of each or all of the compositional values described above for Qassim area seeds.

The rats in the Ex. group underwent a training on a treadmill (IITC Life Science; five-lane rat treadmill), five days/week for eight weeks. A progressive increment in the speed, grade, and duration was adjusted during the first week until the target protocol was achieved, with a speed of 18 m/min and an inclination of 32°, for a two-hour session/day; see Barbier, J, et al., MOL. CELL. BIOCHEM, 2007, 300, 69. An equivalent volume of water was also fed to this group. The fourth group (N.s.Ex.) exposed to both interventions, i.e., Ns feeding and exercise training.

Extraction of the Hearts. After anesthetizing the rats with intraperitoneal injections of 0.2 mL/250 g body weight of ketamine cocktail (60% ketamine, 40% xylazine), the hearts were dissected, cleaned from connective tissue, rinsed, and impeded in cold Ringer's solution. Then, the hearts were blotted dry and weighed. Similarly, the left ventricles were dissected and weighed. The free wall of the left ventricles was extracted and stored in 4% formal saline for histological preparation.

Preparation of the Light Microscopic Slides. After fixation of the left ventricular wall in 4% formal saline, the specimens were shortly washed in water, labeled, and incubated overnight in a tissue processor (Tissue-Tek VIP). The specimens were dehydrated in the following concentrations of alcohol—70%, 90%, and 100% two changes—and two changes of xylene for a period of two hours, respectively. Then, the process of embedding was started by impregnating the specimens in two changes of molten paraffin wax for a period of two hours for each change and one at a temperature of 60° C. The position of the specimens was controlled by cassettes. The prepared blocked tissues were labeled and allowed to solidify. They were then sectioned using microtomy (LEICA RM 2235; Leica BioSystems, Buffalo Grove, IL, USA) at a thickness of 3 μm. The sectioned tissues were floated in warm water and then placed on microscope slides, labeled, and allowed to dry. The sections were dewaxed, washed in water, and stained with hematoxylin & eosin (H&E) or using the following antibodies:

(1) Anti-growth hormone (mouse/rat growth hormone biotinylated affinity purified, goat IgG, R&D system, USA);

(2) Anti-IGF-I antibodies (from Sigma-Aldrich for immunohistochemistry, USA);

(3) Anti-angiotensin-II receptor type I (AT1) antibodies (from Sigma-Aldrich, USA);

(4) Anti-endothelin-I antibodies (ET-1) (from Sigma Aldrich, USA);

(5) Phospho-Akt (S473) pan-specific affinity purified PAb, rabbit IgG (Biocompare);

(6) Phospho-Erk1 (T 202/Y204) Erk2 (T185/Y187) affinity purified PAb, Rabbit IgG (Biocompare).

Estimation of the Antibody Labeling in the Light Microscopic Slides. The immunohistochemical slides of the left ventricular wall were captured using a digital microscope (Coolscope; Nikon Instruments Europe BV, Amsterdam Netherlands). The fields were carefully selected to avoid overlap, freezing defects, gaps, or folds. Ten fields were obtained per specimen per stain or antibody under a power of X400. The photomicrographs were studied using an Image J analyzer.

The cell diameter was considered as the length of the vertical line connecting the cell membranes of the cardiomyocyte and crossing the nucleus. The diameter of 100 cells per specimen was measured, and then the average was calculated.

Figure 1B:
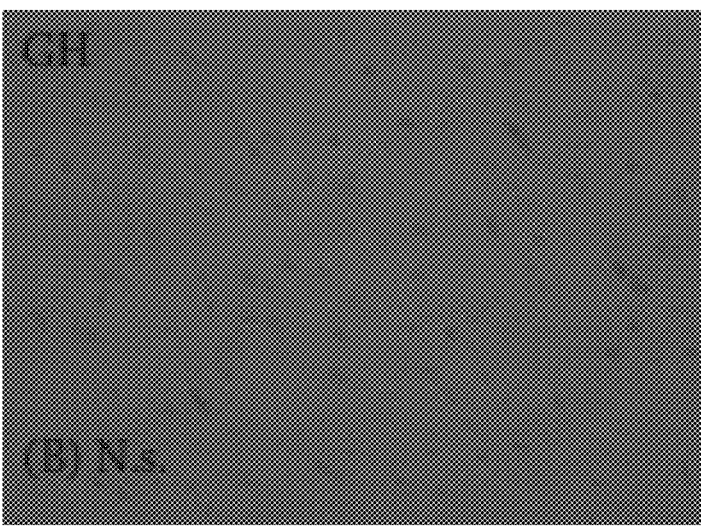
Figure 1C:
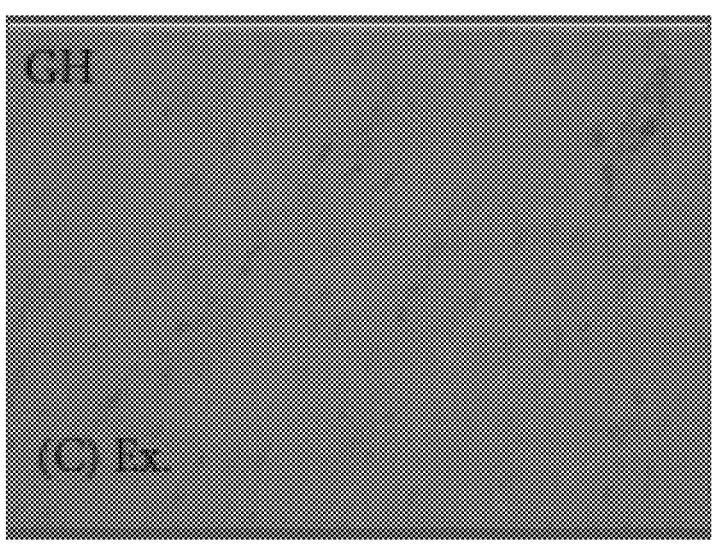
Figure 1D:
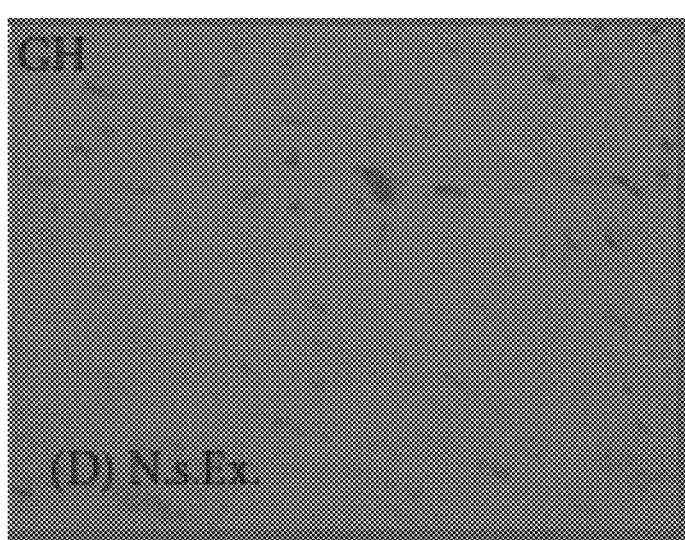
Figure 2A:
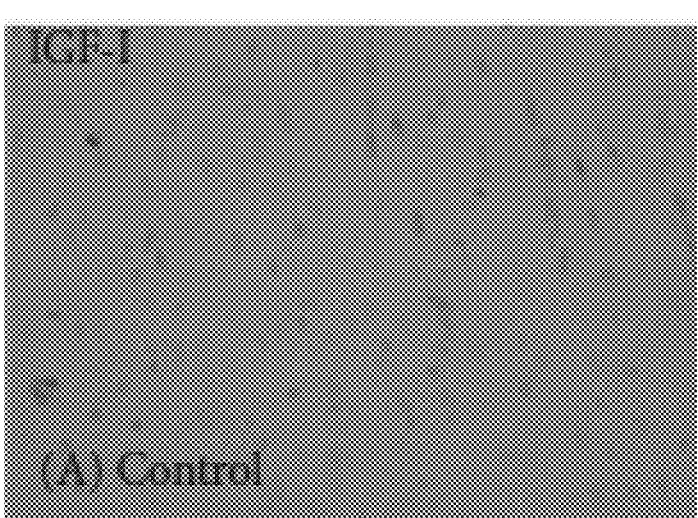
FIGS. 2A-2D. Photomicrographs of the immunohistochemical slides of the left ventricular wall stained with IGF-I: insulin-like growth factor-I; obtained from Control (FIG. 2A) *Nigella sativa* fed group (FIG. 2B), exercise-trained group (FIG. 2C) and *Nigella sativa*, exercise-trained group (FIG. 2D).
Figure 2B:
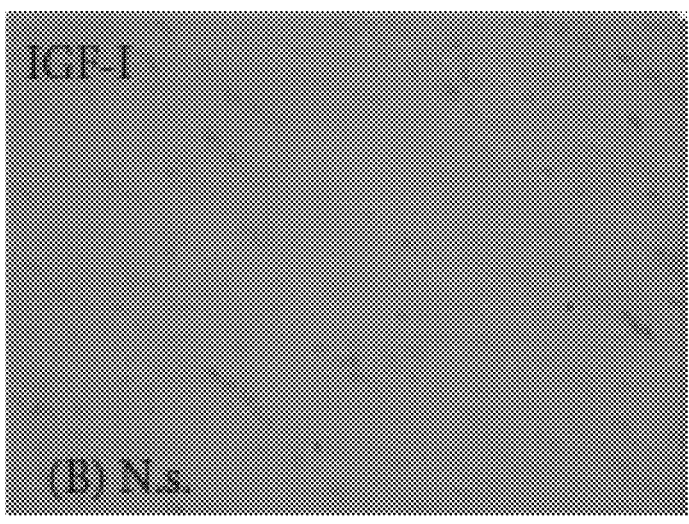
Figure 2C:
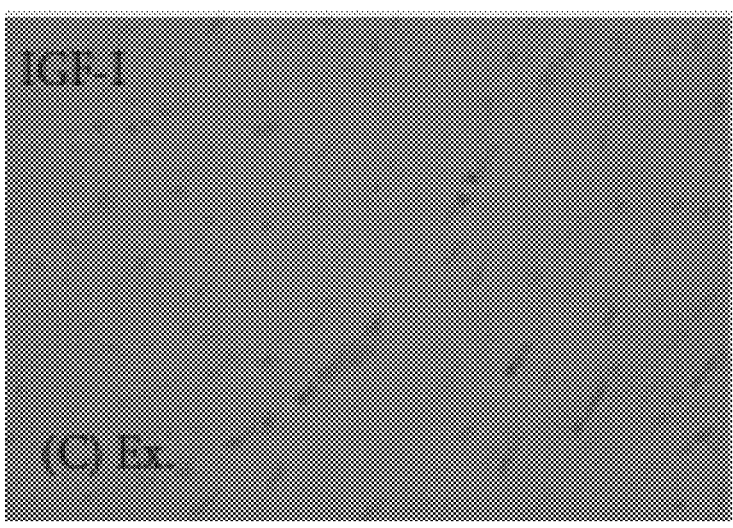
Figure 2D:
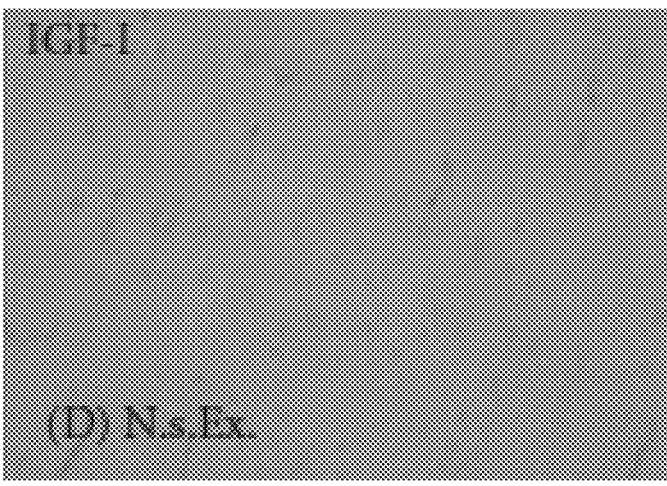
Figure 3A:
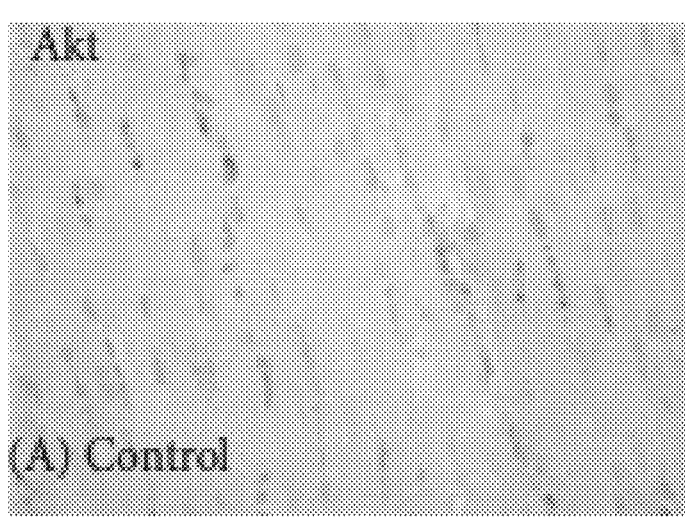
FIGS. 3A-3D. Photomicrographs of the immunohistochemical slides of the left ventricular wall stained with Akt: also known as protein kinase B (PKB) obtained from Control (FIG. 3A) *Nigella sativa* fed group (FIG. 3B), exercise-trained group (FIG. 3C) and *Nigella sativa*, exercise-trained group (FIG. 3D).
Figure 3B:
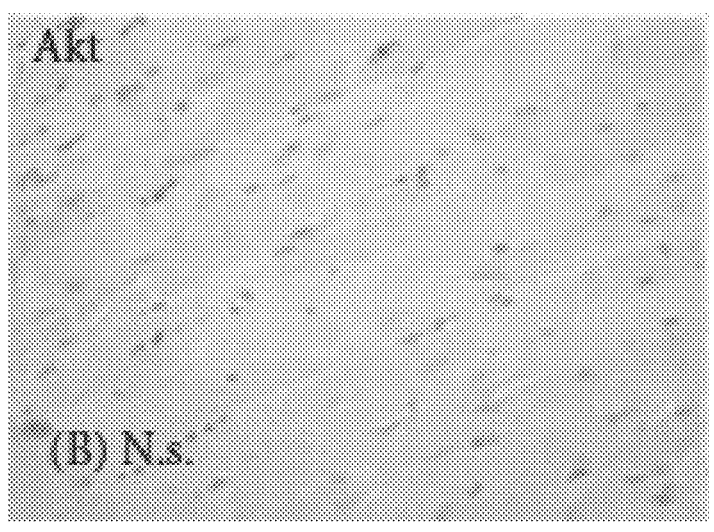
Figure 3C:
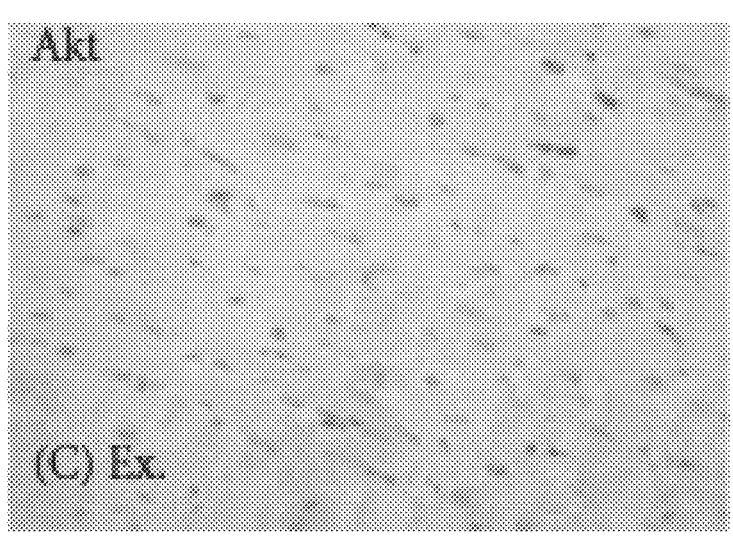
Figure 3D:
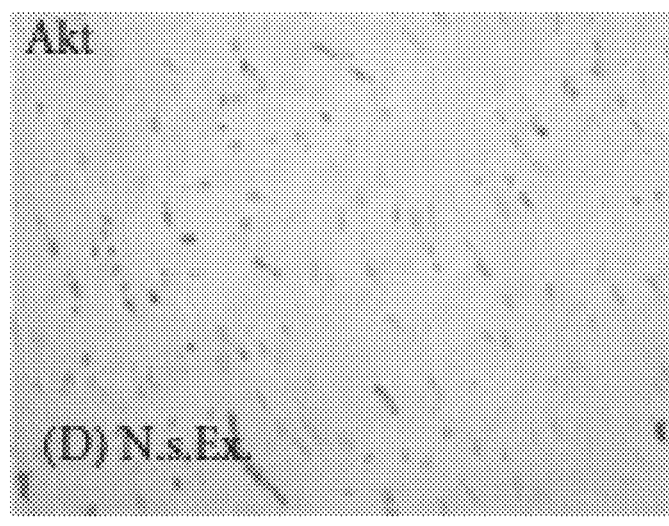
Figure 4A:
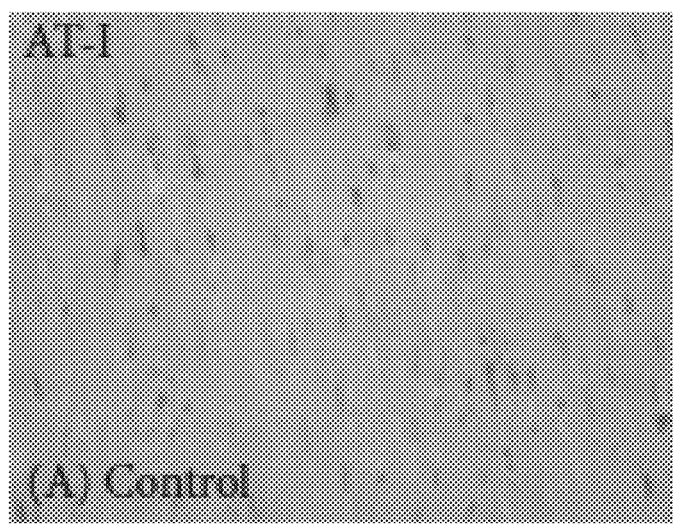
FIGS. 4A-4D: Photomicrographs of the immunohistochemical slides of the left ventricular wall stained with AT-1: angiotensin-II receptor type 1; obtained from Control (FIG. 4A) *Nigella sativa* fed group (FIG. 4B), exercise-trained group (FIG. 4C) and *Nigella sativa*, exercise-trained group (FIG. 4D).
Figure 4B:
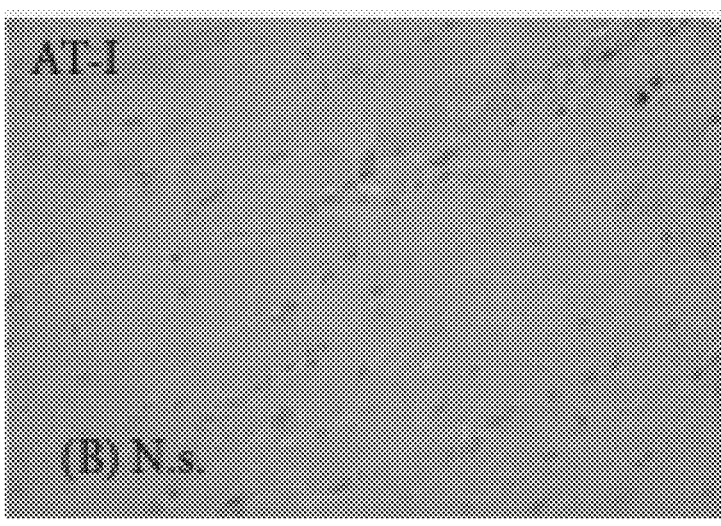
Figure 4C:
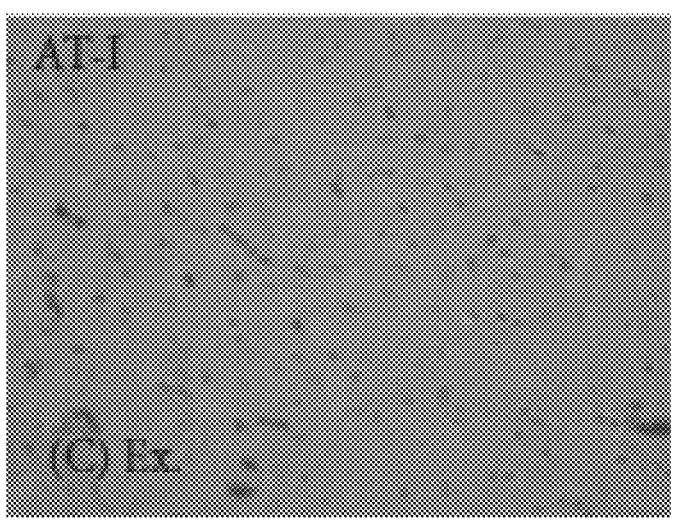
Figure 4D:
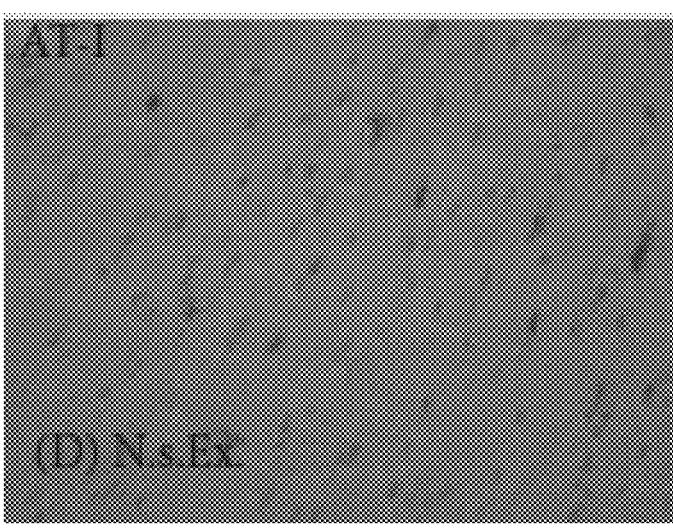
Figure 5A:
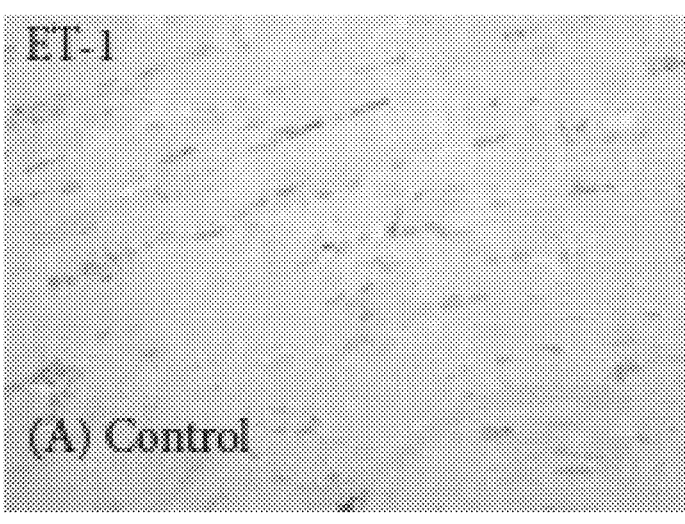
FIGS. 5A-5D: Photomicrographs of the immunohistochemical slides of the left ventricular wall stained with ET-1: endothelin-1 obtained from Control (FIG. 5A), *Nigella sativa* fed group (FIG. 5B), exercise-trained group (FIG. 5C) and *Nigella sativa*, exercise-trained group (FIG. 5D).
Figure 5B:
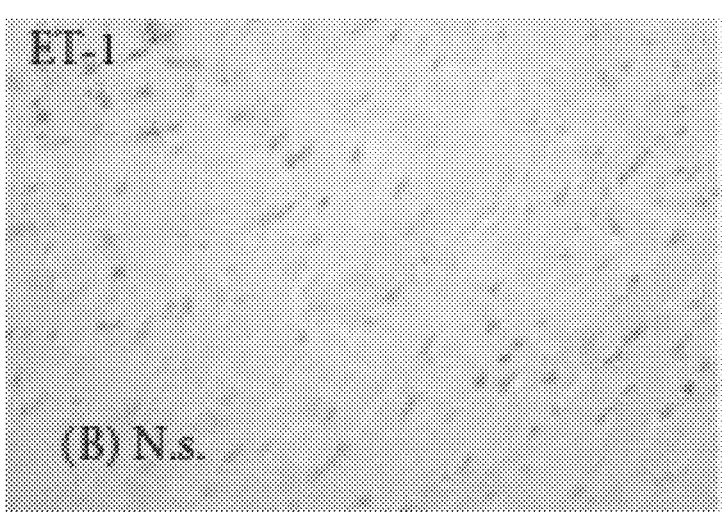
Figure 5C:
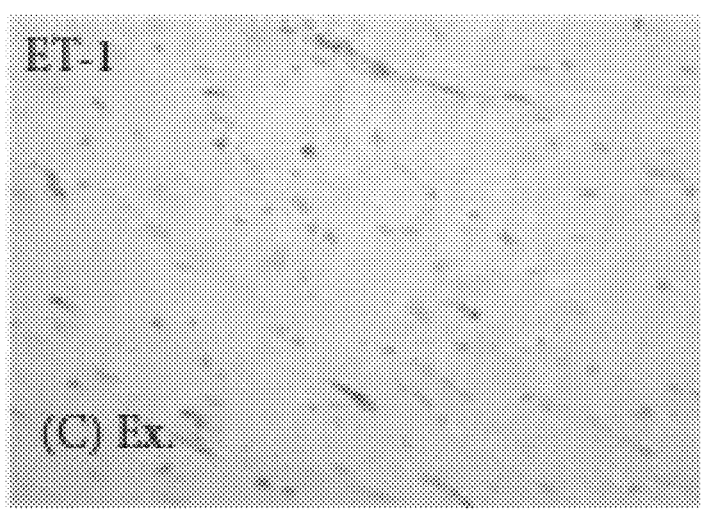
Figure 5D:
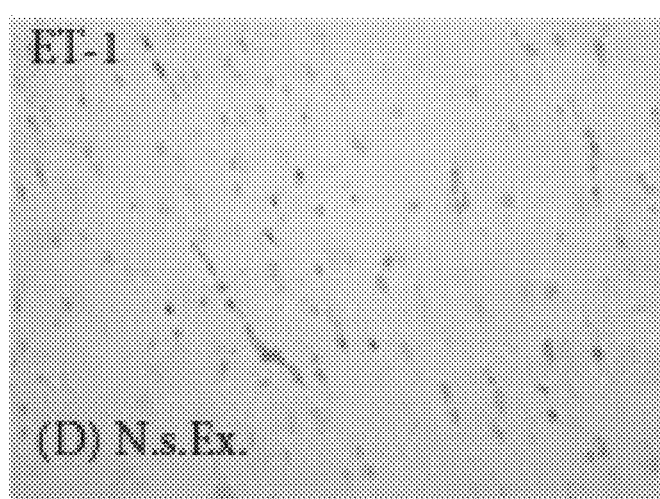
Figure 6A:
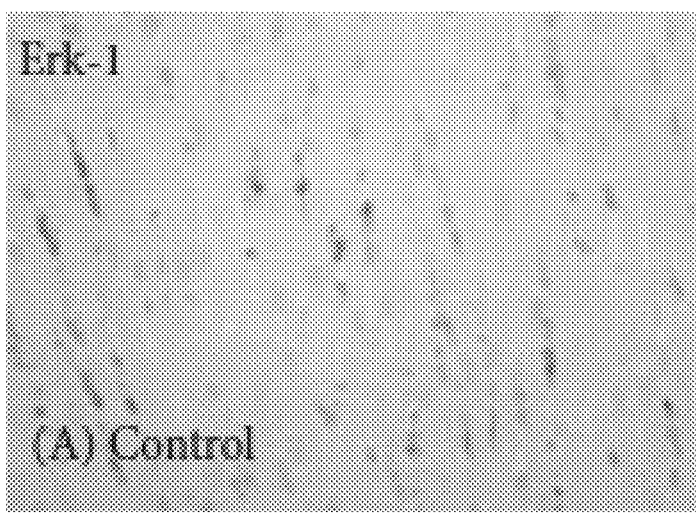
FIGS. 6A-6D: Photomicrographs of the immunohistochemical slides of the left ventricular wall stained with Erk1/2: extracellular signal-regulated kinases ½ obtained from Control (FIG. 6A) *Nigella sativa* fed group (FIG. 6B), exercise-trained group (FIG. 6C) and *Nigella sativa*, exercise-trained group (FIG. 6D).
Figure 6B:
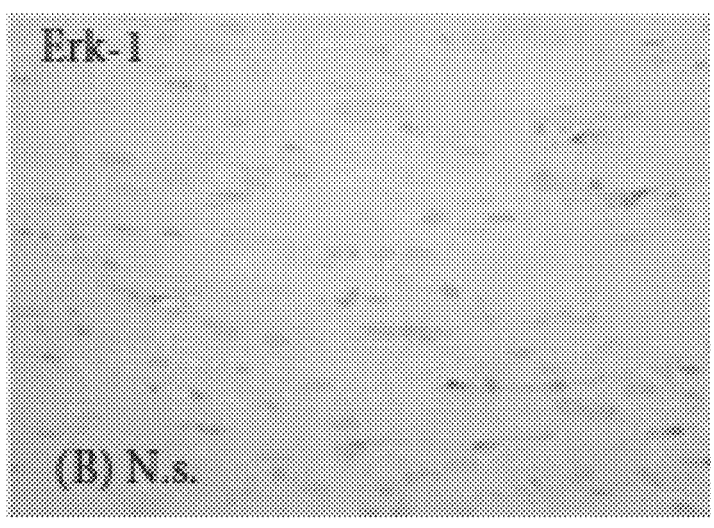
Figure 6C:
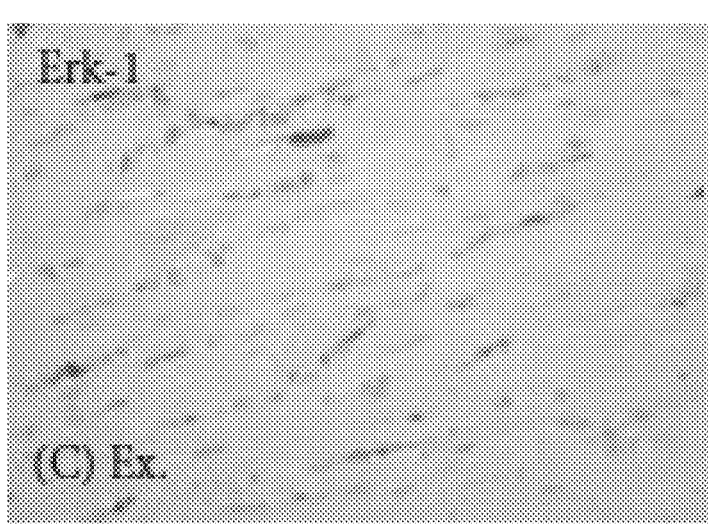
Figure 6D:
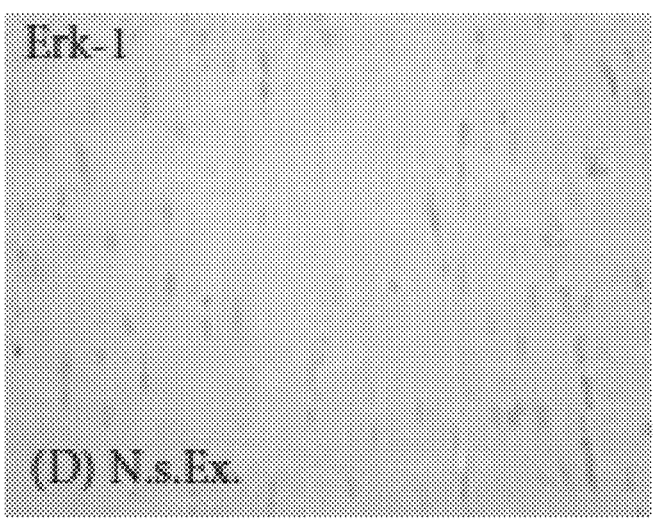

The number of nuclei was counted manually in 10 fields per specimen. For assessing the immune-histochemical slides, the stained area was estimated and then expressed as a ratio of the stained area to the total field area. The mean value of the immunostained area for all fields of a specific antibody in each group was obtained (see FIG. 1 for the photomicrographs of all antibodies).

Statistical Analysis. The data were analyzed using IBM—Statistical analysis software package—SPSS, version 20. All data were expressed as mean±SD and tested by analysis of variance (ANOVA) and LSD post hoc tests to detect any difference between the groups. The level of significance was set at p<0.05.

Photomicrographs representative of the immunohistochemical slides of antibodies obtained from each group are shown in FIG. 1.

The mean value of the cardiomyocyte diameter, the number of nuclei, and the percentage of the stained areas were compared between all the groups, i.e., the control, N.s., Ex., and N.s.Ex. groups using ANOVA and LSD post hoc tests, and the data are presented in Table 3.

nuclei in the microscopic sections of the left ventricular wall of all the experimental groups compared with the controls. This latter finding provides further evidence of growth of cardiac muscle by the methods disclosed herein.

A healthy human adult cardiomyocyte has a cylindrical shape that is approximately 100 pin long and 10-25 pin in diameter. Based on the results above, administration of *Nigella sativa* would increase healthy human cardiomyocyte diameter up to about 11-15%, exercise alone would increase diameter up to about 19-23%, and administration of *Nigella sativa* and exercise up to about 28-32%. Based on the results above, administration of *Nigella sativa* would increase nuclei numbers by up to about 12-16% exercise alone would increase numbers by 14-18% and administration of *Nigella sativa* and exercise would increase numbers up to about 7-11%.

The data herein also evidence an increment in the GH-IGF I-PI3K-AKT1 pathway, which was manifested specifically by the significant increase in GH and the subcellular

TABLE 3

Comparison of the histological and the immunohistochemical findings of the left
ventricular walls among the experimental groups using ANOVA and LSD post hoc test.

|                      | Control           | N.s.                | Ex.                 | N.s. Ex.            |
| -------------------- | ----------------- | ------------------- | ------------------- | ------------------- |
| Cell diameter (μm)   | 88.8 ± 20.9       | 101.1 ± 23.3**      | 108.4 ± 15.5**      | 116.2 ± 9.8**       |
| No. of nuclei        | 191.6 ± 49.2      | 219.2 ± 55.5*       | 223.4 ± 49.8**      | 209.7 ± 54.7**      |
| GH                   | 0.020 ± 0.010     | 0.030 ± 0.013**     | 0.030 ± 0.011**     | 0.031 ± 0.019**     |
| IGF-I                | 0.036 ± 0.025     | 0.045 ± 0.027       | 0.054 ± 0.035**     | 0.045 ± 0.023       |
| Akt                  | 0.0167 ± 0.008    | 0.022 ± 0.015*      | 0.024 ± 0.011*      | 0.027 ± 0.012**     |
| AT-1                 | 0.021 ± 0.011     | 0.021 ± 0.012       | 0.030 ± 0.020**     | 0.026 ± 0.010       |
| ET-1                 | 0.019 ± 0.011     | 0.020 ± 0.012       | 0.026 ± 0.016*      | 0.016 ± 0.010       |
| ErK1/2               | 0.039 ± 0.20      | 0.021 ± 0.012**     | 0.024 ± 0.011**     | 0.017 ± 0.010**     |

*p < 0.05.
**p < 0.01. ap < 0.05 compared to these exercise group.
GH: growth hormone;
IGF-I: insulin-like growth factor-I;
Akt: also known as protein kinase B (PKB);
AT-1: angiotensin-II receptor type 1;
ET-1: endothelin-1;
Erk1/2: extracellular signal-regulated kinases ½.
GH, IGF-1, Akt. AT-1, ET-1, and ErK1/2 expressed as a ratio of the stained area to the total field area.

Cardiomyocyte diameter, number of nuclei, GH, and Akt were significantly higher in all the experimental groups—N.s., Ex., and N.s.Ex. groups—than the control group.

IGF-I, angiotensin-II receptor type 1 (AT-1), and endothelin-1 (ET-1) were significantly higher only in Ex. rats only compared with the control group.

Erk1/2 was significantly lower in all experimental groups compared with the control group.

Histopathological Examination. Histopathological examination of H&E-stained sections of the left ventricular tissue of all the groups revealed a comparable normal structure and integrity of the cardiomyocytes. The cardiomyocytes appeared in these sections as faintly striated and multinucleated. There were no signs of inflammation or collagen fiber deposition in any of the experimental sections compared with the control apart from the increase in cardiomyocyte diameter and number of nuclei stated earlier in the previous paragraph.

These data reveal some of the molecular mechanisms underlying *Nigella sativa* induced cardiac hypertrophy and compare them to that induced by exercise alone.

The inventors demonstrate herein a comparable significant increase in the cardiomyocyte diameter in N.s. rats, Ex. rats, and N.s. Ex rats compared with the controls, as significant increases in the numbers of the cardiomyocyte enzyme Akt but without evidence of a significant rise in IGF-1. This pathway has been frequently affirmed as the main pathway responsible for mediating the physiological cardiac hypertrophy induced by exercise training; Weeks, K. I. et al ADV. EXP. MED. BIOL., 2017, 100, 187; Bo, B. et al., BIOMOLECULES, 2020, 11(1). In some embodiments increments in the GH-IGF I-PI3K-AKT1 pathway may be characterized by a rise in GH by 5, 10, 15, 20, 25, 30, 35, 40, 45, 50 or >50% compared to controls not receiving *Nigella sativa* or a rise in IGF-1 by 5, 10, 15, 20, 25, or >25% compared to controls not receiving *Nigella sativa*. Other indicia of increments to the GH-IGF I-PI3K-AKT1 pathway include increases in Akt by 5, 10, 15, 20, 25, 30, 35, 40, 45, 50 or >60% and/or decreases in ErK1/2 by 5, 10, 15, 20, 25, 30, 35, 40, 45, 50, 55 or >55% as determined as described for values in Table 3.

GH action is mediated via the release of IGF-I from various tissues such as the liver, the myocardium, and the skeletal muscle. IGF-I, which is a peptide similar to insulin in structure, is released in the myocardium in a paracrine mode, binds to transmembrane tyrosine receptors in the cardiomyocytes, and provokes the activation of PI3K-Akt pathway to mediate the hypertrophy of the heart; DeBosch, B., CIRCULATION, 2006, 113(16), 2097. Experimentally, the application of IGF-I on a culture of adult cardiomyocytes induces hypertrophy of the cells, increases myofibril proteins, promotes the synthesis of new sarcomeres, and upregulates its receptors. Administration of GH, IGF-I, or a combination of both factors to rats or mice elicited concentric cardiac hypertrophy manifested by an increase of the cardiac index and the myocyte diameter without significant increase in fibrosis, in addition to an increase in the myocardial contractility; Cittadini, A., et al., CIRCULATION, 1996, 93(4), 800; Tanaka, N., et al., AM. J. PHYSIOL. HEART CIRC. PHYSIOL, 1998, 275(2), H393.

IGF-I was significantly elevated in the Ex. group, whereas it was equivalent to the controls in N.s. and N.s.Ex groups despite the documented cardiac hypertrophy in these groups. While not being bound to any particular explanation or theory, Ns administration might culminate in the upregulation of an analogue of IGF-I to mediate activation of the GH-IGF I-PI3K-Akt pathway. The IGF-I superfamily (IGF-I, IGF-II, insulin) possesses a great overlap and crosstalk in both the function and the structure; Werner, H., et al., ARCH. PHYSIOL. BIOCHEM. 2008, 114(1), 17.

Akt is the subcellular enzyme involved in the GH-IGF I-PI3K-Akt pathway. Akt was elevated in all the experimental groups compared to controls consistent with induction of physiological (non-pathological) cardiac hypertrophy in these groups by either exercise or administration of *Nigella sativa*. This is consistent with evidence that Akt is required for physiological cardiac growth; DeBosh, et al., CIRCULATION, 2006, 113(17), 2097.

It was found that AT-1 and ET-I were significantly elevated in the Ex. group only and not in groups receiving *Nigella sativa* or the control group. However, Erk1/2 was significantly reduced in all the experimental groups (N.S., Ex., and N.s.Ex.) compared with the control group.

The role of the GH-IGF-I-PI3K pathway has been associated with induction of physiological cardiac hypertrophy but high levels of AT-1 and endothelin-1 are associated with pathological cardiac hypertrophy via the GPCR pathway. Thus, the results in Table 3 showing higher levels of AT-1 and endothelin 1 in exercising subjects were surprising as these high levels are inconsistent with physiological cardiac hypertrophy.

The inventors consider that these results show that both pathways can be active simultaneously especially in athletes subject to strenuous of prolonged exercise as modelled by the treadmill results in the two exercised groups reported in Table 3

The pathological component associated with high levels of AT-1 and endothelin may occur by decompensation of the heart to cope with functional overload resulting from too intense exercise, for example, For example, in exercise-induced cardiac hypertrophy and deterioration of the cardiac function in competitive sport athletes, Saari, M. J. et al., HEART, LUNG AND CIRCULATION, 2018, 27(9), 1052; and sudden cardiac arrest and fatal arrhythmias are often encountered in long-distance runners; Kim, J. H. et al., NEW ENGL J. MED, 2012, 366(2), 130. Vigorous or prolonged exercise activity frequently incurs the activation of pathological cardiac pathways and yields elevated biomarkers of cardiac damage, Cunningham, T. et al., CARDIOLOGY IN THE YOUNG, 2017, 27(S1), S94. Furthermore, some competitive long-distance runners developed exercise-induced hypertension, which was associated with an abnormal level of angiotensin-II; Kim, C. H., et al., MEDICINE, 2020, 99(27), e20943. ET-1 was also found elevated significantly in the Ex. group compared with controls. ET-1 might also contribute to the conversion of the exercise-induced cardiac hypertrophy into pathological remodeling at extensive strenuous exercise. Iemitsu et al.

reported high ET-1 levels in rats after 8 weeks of treadmill training but not after 4 weeks of training; Iemitsu, et al., Exp. BIOL. MED, 2006, 231(6), 871.

Table 3 also shows that non-exercised animals receiving *Nigella sativa* did not produce significantly higher levels of AT-1 or endothelin-1 that controls indicating that *Nigella sativa* does not trigger pathological hypertrophy. Similarly, exercised animals receiving *Nigella sativa* produced less AT-1 and endothelin 1 that exercised animals not receiving *Nigella sativa* indicating that *Nigella sativa* inhibits release of these precursors to the pathological pathway. For example, increases or decreases in AT-1 and ET-1 levels or expression may be no more than 1, 2, 3, 4, or 5% compared to controls not receiving *Nigella sativa*.

As mentioned above, AT-1 and ET-1 were not elevated in the N.s.Ex. group, which underwent the same exercise protocol as that of the Ex. group. This surprising finding describes a beneficial adaptive response for long-term administration of *Nigella sativa* through its ability to block the exercise-induced upregulation of AT-1 and ET-1. It also reflects that the *Nigella sativa*-induced cardiac hypertrophy is a safer and healthier model than that induced by exercise training. Therefore, Ns supplements are recommended for cardiovascular protection particularly for vulnerable candidates such as those involved in highly competitive sports or others subject to conditions producing pathological cardiac hypertrophy.

Erk1/2 was found to be reduced in all the experimental groups compared with controls. However, the reduction of Erk1/2 was more pronounced in the N.s.Ex. group. The rats used in these studies exhibited increases in AT-1 and endothelin, so a reduction in Erk1/2 was unexpected. These results are consistent with Ns- and exercise-induced cardiac hypertrophies being classed as physiological forms of cardiac hypertrophy.

As shown by the data above, regular or long-term administration of *Nigella sativa* induces physiological cardiac hypertrophy resulted in an increase in cardiomyocyte diameter and the numbers of cardiomyocyte nuclei. This type of cardiac hypertrophy also known as physiological hypertrophy is mediated via the GH-IGF I-PI3KAkt pathway as reflected by the significant elevations of GH and Akt.

Administration of *Nigella sativa* to subjects undergoing vigorous exercise hinders the adverse responses generated by the vigorous exercise and blocks the undesirable provocation of G-protein coupled receptor (GPCR) pathway associated with pathogenicity. Moreover, the synergistic favorable effects of Ns feeding coupled with exercise training can be recommended as a prophylactic or therapeutic strategy for vulnerable individuals such as elite athletes.

Terminology used herein is for the purpose of describing particular embodiments only and is not intended to be limiting of the invention.

The following abbreviations are used herein:

Ns: *Nigella sativa*
N.s.: *Nigella sativa*-fed group
Ex.: Exercise-trained group
N.s.Ex.: *Nigella sativa*-fed exercise-trained group
GH: Growth hormone
IGF-1: Insulin-like growth factor-I
PI3K: Phosphoinositide 3-kinase
Akt: Also known as protein kinase B (PkB)
GPCR: G-protein-coupled receptors
AT-1: Angiotensin-II receptor type 1
ET-1: Endothelin-1
MAPK: Mitogen-activated protein kinase
Erk1/2: Extracellular signal-regulated kinases 1/2

ANOVA: Analysis of variance

LSD: Least significant difference

SD: Standard deviation.

As used herein, the singular forms "a", "an" and "the" include the plural forms as well, unless the context clearly indicates otherwise.

It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

As used herein, the term "and/or" includes any and all combinations of one or more of the associated listed items and may be abbreviated as "/".

As used herein in the specification and claims, including as used in the examples and unless otherwise expressly specified, all numbers may be read as if prefaced by the word "substantially", "about" or "approximately," even if the term does not expressly appear. The phrase "about" or "approximately" may be used when describing magnitude and/or position to indicate that the value and/or position described is within a reasonable expected range of values and/or positions.

A value that is "substantially", "about" or "approximately" of a stated value, unless otherwise specified, may be +/−0.1% of the stated value (or range of values), +/−0.2% of the stated value (or range of values), +/−0.5% of the stated value (or range of values), +/−1% of the stated value (or range of values), +/−2% of the stated value (or range of values), +/−5% of the stated value (or range of values), +/−10% of the stated value (or range of values), +/−15% of the stated value (or range of values), +/−20% of the stated value (or range of values).

Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10 it also describes subranges for Parameter X including 1-9, 1-8, 1-7, 2-9, 2-8, 2-7, 3-9, 3-8, 3-7, 2-8, 3-7, 4-6, or 7-10, 8-10 or 9-10 as mere examples. A range encompasses its endpoints as well as values inside of an endpoint, for example, the range 0-5 includes 0, >0, 1, 2, 3, 4, <5 and 5.

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

As referred to herein, all compositional percentages are by weight of the total composition, unless otherwise specified.

As used herein, the word "include," and its variants, is intended to be non-limiting, such that recitation of items in a list is not to the exclusion of other like items that may also be useful in the materials, compositions, devices, and methods of this technology.

Similarly, the terms "can" and "may" and their variants are intended to be non-limiting, such that recitation that an embodiment can or may comprise certain elements or features does not exclude other embodiments of the present invention that do not contain those elements or features.

All publications and patent applications mentioned in this specification are herein incorporated by reference in their entirety to the same extent as if each individual publication or patent application was specifically and individually indicated to be incorporated by reference, especially referenced is disclosure appearing in the same sentence, paragraph, page or section of the specification in which the incorporation by reference appears.

The citation of references herein does not constitute an admission that those references are prior art or have any relevance to the patentability of the technology disclosed herein. Any discussion of the content of references cited is intended merely to provide a general summary of assertions made by the authors of the references, and does not constitute an admission as to the accuracy of the content of such references.

The invention claimed is:

1. A method for reducing a severity of pathological cardiac hypertrophy, comprising:
   identifying a subject having pathological cardiac hypertrophy,
   administering daily to the subject 800 mg per kg of body weight of the subject Nigella sativa for 8 weeks; and
   exercising the subject five days per week of the eight weeks,
   wherein the administering induces physiological cardiac hypertrophy in the subject,
   wherein the Nigella sativa is orally administered,
   wherein the subject is an athletic male having 5-10% body fat and an average heart rate of 49-55 beats per minute,
   wherein the exercising comprises vigorous exercising at 70 to 85% of the subject's maximum heart rate, wherein maximum heart rate is calculated by subtracting the subject's age from 220,
   wherein the administering and exercising increases a cardiomyocyte diameter in the subject 28-32% compared to a subject that is not administered Nigella sativa and does not perform exercise, and
   wherein following the administering and exercising angiotensin-II receptors 1 (AT-1) and endothelin-1 (ET-1) levels in the subject differ no more than 5% compared to a subject that is not administered Nigella sativa and does not perform exercise.

2. The method of claim 1, wherein the subject has pressure stress overload caused by hypertension, valvular heart disease, valvular injury, or injury of the cardiac muscle due to ischemia and infarction.

3. The method of claim 1, wherein the subject has hypertension characterized by blood pressure of higher than 140/90.

4. The method of claim 1, wherein the subject is diabetic or pre-diabetic and has an A1C (percent) of 5.7% or more, a fasting plasma glucose of 100 or more, and/or an oral glucose tolerance test value of 200 or above.

5. The method of claim 1, wherein the Nigella sativa is administered no more than two hours before the exercising; or wherein the Nigella sativa is administered no more than two hours after the exercising.

6. The method of claim 1, further comprising administering an AKT antagonist or an Erk1/2 antagonist.

7. The method of claim 1, further comprising administering an angiotensin-II receptor antagonist and/or administering an endothelin-1 receptor antagonist.

8. The method of claim 1, wherein the exercising is for two hours each day.

9. The method of claim 1, wherein following the administering and exercising IGF-1 levels in the subject differ no more than 5% compared to a subject that is not administered *Nigella sativa* and does not perform exercise.

\* \* \* \* \*